US011851717B2

(12) United States Patent
Hancock et al.

(10) Patent No.: US 11,851,717 B2
(45) Date of Patent: Dec. 26, 2023

(54) DIAGNOSTIC FOR SEPSIS

(71) Applicant: Robert E. W. Hancock, Vancouver (CA)

(72) Inventors: Robert E. W. Hancock, Vancouver (CA); Olga M. Pena Serrato, Coquitlam (CA); David G. Hancock, Vancouver (CA); John Boyd, Vancouver (CA)

(73) Assignee: Robert E. W. Hancock, Vancouver (CA)

( * ) Notice: Subject to any disclaimer, the term of this patent is extended or adjusted under 35 U.S.C. 154(b) by 0 days.

(21) Appl. No.: 16/279,788

(22) Filed: Feb. 19, 2019

(65) Prior Publication Data

US 2020/0032321 A1 Jan. 30, 2020

Related U.S. Application Data

(63) Continuation of application No. 15/124,333, filed as application No. PCT/CA2015/000160 on Mar. 13, 2015, now abandoned.

(60) Provisional application No. 61/953,458, filed on Mar. 14, 2014.

(51) Int. Cl.
| | |
|---|---|
| *C12Q 1/68* | (2018.01) |
| *C07H 21/04* | (2006.01) |
| *C12Q 1/689* | (2018.01) |
| *C12Q 1/6883* | (2018.01) |
| *A61K 35/15* | (2015.01) |
| *C12N 15/10* | (2006.01) |

(52) U.S. Cl.
CPC .............. *C12Q 1/689* (2013.01); *A61K 35/15* (2013.01); *C12N 15/1068* (2013.01); *C12Q 1/6883* (2013.01); *C12Q 2600/118* (2013.01); *C12Q 2600/136* (2013.01); *C12Q 2600/158* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 7,767,395 B2 | 8/2010 | Garrett et al. | |
| 8,029,982 B2 | 10/2011 | Kingsmore et al. | |
| 10,533,224 B2 | 1/2020 | Khatri et al. | |
| 2009/0203534 A1 | 8/2009 | Hossain et al. | |
| 2011/0076685 A1 | 3/2011 | Moeller et al. | |
| 2011/0312521 A1 | 12/2011 | Chaussabel | |
| 2013/0316337 A1* | 11/2013 | Aird .................... | C12Q 1/6883 435/6.11 |
| 2014/0162370 A1* | 6/2014 | Ling .................... | G01N 33/6893 436/86 |
| 2016/0055295 A1* | 2/2016 | Brandon ................ | G16B 25/00 514/789 |
| 2016/0244834 A1* | 8/2016 | Ong ..................... | C12Q 1/6883 |
| 2020/0131577 A1 | 4/2020 | Khatri et al. | |

FOREIGN PATENT DOCUMENTS

| | | | |
|---|---|---|---|
| CA | 2745189 A1 * | 7/2010 | ........... C12Q 1/6883 |
| CN | 101208602 | 6/2008 | |
| EP | 1950310 A1 | 7/2008 | |
| EP | 2520662 A1 | 11/2012 | |
| WO | WO 2009095786 | 6/2009 | |
| WO | WO 2010049818 | 6/2010 | |
| WO | WO2014209238 | 12/2012 | |
| WO | WO2013152047 | 10/2013 | |

OTHER PUBLICATIONS

Calvano et al. (Nature, vol. 437, vol. 13, pp. 1032-1037, Oct. 2005 (Year: 2005).*
Pena et al. (J. of Immunology, vol. 186, May 15, 2011) (Year: 2011).*
Tang et al. (Critical Care, vol. 14, R237, 2010) (Year: 2010).*
Roberts et al. (Clin Pharmacokinet, vol. 45, No. 8, pp. 755-773, 2006). (Year: 2006).*
Tom van der Poll (Immunotherapy of sepsis, The Lancet Infectious diseases, vol. 1, 2001, pp. 165-174). (Year: 2001).*
Calvano et al., (2005) "A network . . . based analysis of systemic inflammation in humans", Nature, 437(13):1032-1037.
Pena et al., (2011) "Endotoxin Tolerance Represents a Distinctive State of Alternative Polarization (M2) in Human Mononuclear Cells", J. of Immunology, 186:1-13.
A Sica and A Mantovani, "Macrophage plasticity and polarization: in vivo veritas" Journal of Clinical Investigation 2012, 122, 787-795.
A Sutherland, M Thomas, RA Brandon, RB Brandon, J Lipman, B Tang, A McLean, R Pascoe, G Price, T Nguyen, G Stone and D Venter, "Development and validation of a novel molecular biomarker diagnostic test for the early detection of sepsis" *Critical Care* 2011, 15:R149.
Antibiotic therapy for sepsis, Cao Shuhua et al., Sepsis manual, Jilin science and Technology Press, 2005.07 version 1 p. 64-91.
<in Chinese—OA + English translation of OA provided>.
C Del Fresno et al., "Potent phagocytic activity with impaired antigen presentation identifying lipopolysaccharide-tolerant human monocytes: demonstration in isolated monocytes from cystic fibrosis patients" Journal of Immunology 2009, 182:10, 6494-6507.

(Continued)

*Primary Examiner* — Jeanine A Goldberg
(74) *Attorney, Agent, or Firm* — Mandar A. Joshi; Bozicevic, Field & Francis LLP

(57) ABSTRACT

A method of diagnosing severe sepsis prior to definitive clinical diagnosis. A pattern of gene expression that correlates strongly with a future diagnosis of severe sepsis and organ failure was identified in patients who had their blood drawn at first clinical presentation. The methods comprise identifying a pattern of two or more polynucleotides, whereby the altered expression of these polynucleotides correlates with prospective and actual sepsis. Also methods of identifying agents for treating sepsis based on the characteristics of this gene expression pattern are provided.

14 Claims, 8 Drawing Sheets

(56) References Cited

OTHER PUBLICATIONS

C Pierrakos and J-L Vincent, "Sepsis biomarkers: A review" Critical Care, 2010, vol. 14, R15.

DM Maslove and HR Wong, "Gene expression profiling in sepsis: timing, tissue, and translational considerations" Trends in Molecular Medicine 20:4, 204-213, Published Online Feb. 15, 2014.

G Terrin, A Passariello, M De Curtis, R Paludetto and RB Canani, "S100 A8/A9 protein as a marker for early diagnosis of necrotizing enterocolitis in neonates" Arch Dis Child 2012, 97:12, 1102.

GP Otto, M Sossdorf, RA Claus, J Rödel, K Menge, K Reinhart, M Bauer and NC Riedemann, "The late phase of sepsis is characterized by an increased microbiological burden and death rate" Critical Care 2011, 15:4, R183.

HR Wong, TP Shanley, B Sakthivel, N Cvijanovich, R Lin, GL Allen, NJ Thomas, A Doctor, M Kalyanaraman, NM Tofil, S Penfil, M Monaco, MA Tagavilla, K Odoms, K Dunsmore, M Barnes, BJ Aronow, and Genomics of Pediatric SIRS/Septic Shock Investigators, "Genome-level expression profiles in pediatric septic shock indicate a role for altered zinc homeostasis in poor outcome" Physiol Genomics 2007 30:2, 146-155.

HR Wong, N Cvijanovich, GL Allen, R Lin, N Anas, K Meyer, RJ Freishtat, M Monaco, K Odoms, B Sakthivel, TP Shanley, and Genomics of Pediatric SIRS/Septic Shock Investigators, "Genomic expression profiling across the pediatric systemic inflammatory response syndrome, sepsis, and septic shock spectrum" Crit Care Med 2009, 37:5, 1558-1566.

IN Shalova, JY Lim, M Chittezhath, AS Zinkernagel, F Beasley, E Hernández-Jiménez, V Toledano, C Cubillos-Zapata, A Rapisarda, J Chen, K Duan, H Yang, M Poidinger, G Melillo, V Nizet, F Arnalich, E López-Collazo, and SK Biswas, "Human monocytes undergo functional re-programming during sepsis mediated by hypoxia-inducible factor-1α" Immunity 2015, 42, 484-498.

JC Schefold, D Hasper, HD Volk, P Reinke, "Sepsis: Time has come to focus on the later stages" Medical Hypotheses 2008, 71:2, 203-208.

JL Wynn, NZ Cvijanovich, GL Allen, NJ Thomas, RJ Freishtat, N Anas, K Meyer, PA Checchia, R Lin, TP Shanley, MT Bigham, S Banschbach, E Beckman, and HR Wong, "The influence of developmental age on the early transcriptomic response of children with septic shock" Mol Med 2011, 17:11-12, 1146-1156.

JM Murkin and KR Walley, "Genetic susceptibility to inflammatory injury and various adverse outcomes" The Journal of Extra-Corporeal Technology 2009, 41:1 p. 43-p. 49.

J-M Cavaillon, C Adrie, C Fitting and M Adib-Conquy, "Reprogramming of circulatory cells in sepsis and SIRS" J Endotoxin Res 2005; 11:5, 311-320.

J-M Cavaillon and M Adib-Conquy, "Bench-to-bedside review: Endotoxin tolerance as a model of leukocyte reprogramming in sepsis" Critical Care Medicine 2006, 10:5, 233.

LC Parker, EC Jones, LR Prince, SK Dower, MKB Whyte and I Sabroe, "Endotoxin tolerance induces selective alterations in neutrophil function" J Leukocyte Biology 2005, 78:6, 1301-1305.

L-N Zhang, X-H Wang, L Wu, L Huang, C-G Zhao, Q-Y Peng, Y-H Ai, "Diagnostic and predictive levels of calcium-binding protein A8 and tumor necrosis factor receptor-associated factor 6 in sepsis-associated encephalopathy: A prospective observational study" Chinese Medical Journal 2016, 129:14, 1674-1681.

M Heusinkveld, PJ de Vos van Steenwijk, R Goedemans, TH Ramwadhdoebe, A Gorter, MJP Welters, T van Hall and SH van der Burg, "M2 Macrophages Induced by Prostaglandin E2 and IL-6 from Cervical Carcinoma Are Switched to Activated M1 Macrophages by CD4+ Th1 Cells" Journal of Immunology 2011, 187:3, 1157-1165.

M Suárez-Santamaría, F Santolaria, A Pérez-Ramirez, M-R Alemán-Valls, A Martínez-Riera, E González-Reimers, M-J de la Vega and A Milena, "Prognostic value of inflammatory markers (notably cytokines and procalcitonin), nutritional assessment, and organ function in patients with sepsis" Eur Cytokin Netw. 2010, 21:1, 19-26.

M van der Flier, EM Baerveldt, A Miedema, NG Hartwig, JA Hazelzet, M Emonts, R de Groot, EP Prens, AJ van Vught, and NJ Jansen, "Decreased expression of serum and microvascular vascular endothelial growth factor receptor-2 in Meningococcal sepsis" Pediatr Crit Care Med 2013, 14:7, 682-685.

N Cvijanovich, TP Shanley, R Lin, GL Allen, NJ Thomas, P Checchia, N Anas, RJ Freishtat, M Monaco, K Odoms, B Sakthivel and HR Wong, "Validating the genomic signature of pediatric septic shock" Physiol Genomics 2008, 34, 127-134.

NH Lyle, OM Pena, JH Boyd, and REW Hancock, "Barriers to the effective treatment of sepsis: antimicrobial agents, sepsis definitions, and host-directed therapies" Ann. N.Y. Acad. Sci. 2014, 1323, 101-114.

OM Pena, DG Hancock, NH Lyle, A Linder, JA Russell, J Xia, CD Fjell, JH Boyd and REW Hancock, "An endotoxin tolerance signature predicts sepsis and organ dysfunction at initial clinical presentation" EBioMedicine 2014, 1, 64-71.

R Pankla, S Buddhisa, M Berry, DM Blankenship, GJ Bancroft, J Banchereaut, G Lertmemongkolchai and D Chaussabel, "Genomic transcriptional profiling identifies a candidate blood biomarker signature for the diagnosis of septicemic melioidosis" Genome Biology 2009 10:R127.

RS Hotchkiss, G Monneret and D Payen, "Immunosuppression in sepsis: a novel understanding of the disorder and a new therapeutic approach" Lancet Infectious Diseases 2013, 13:3, 260-268.

S Wang, R Song, Z Wang, Z Jing, S Wang and J Ma, "S100A8/A9 in inflammation" Front Immunol. 2018, 9, 1298.

TP Shanley, N Cvijanovich, R Lin, GL Allen, NJ Thomas, A Doctor, M Kalyanaraman, NM Tofil, S Penfil, M Monaco, K Odoms, M Barnes, B Sakthivel, BJ Aronow, and HR Wong, "Genome-level longitudinal expression of signaling pathways and gene networks in pediatric septic shock" Mol Med 2007, 13:9-10, 495-508.

Y Ma, D Vilanova, K Atalar, O Delfour, J Edgeworth, M Ostermann, M Hernandez-Fuentes, S Razafimahatratra, B Michot, DH Persing, I Ziegler, B Törös, P Mölling, P Olcén, R Beale and GM Lord, "Genome-wide sequencing of cellular micrornas identifies a combinatorial expression signature diagnostic of sepsis" PLoS ONE 2013, 8:10, e75918.

Bone et al., "Definitions for sepsis and organ failure and guidelines for the use of innovative therapies in sepsis" Chest 1992, 101:6, 1644-1655.

Kumar et al., "Duration of hypotension before initiation of effective antimicrobial therapy is the critical determinant of survival in human septic shock" Crit Care Med 2006, 34:6, 1589-96.

Marshall, "Why have clinical trials in sepsis failed?" Trends Mol Med 2014 20:4, 195-203.

Maslove et al., "Identification of sepsis subtypes in critically ill adults using gene expression profiling" Crit Care 2012, 16:5, R183.

Lindig et al., (2013) "Age-independent co-expression of antimicrobial geneclusters in the blood of septic patients" International Journal of Antimicrobial Agents, 42:1-13.

Madsen-Bouterse et al., (2010) "The Transcriptome of the Fetal Inflammatory Response Syndrome" Am. J. Reprod. Immunol., 63(1):73-92.

Prucha et al., (2004) "Expression Profiling: Toward an Application In Sepsis Diagnostics" SHOCK, 22(1):29-33.

Tang et al., (2009) "Gene-expression profiling of peripheral blood mononuclear cells in sepsis*" Crit Care Med, 37(3):882-888.

Wong et al., (2012) "The pediatric sepsis biomarker risk model" Critical Care, 16:1-9.

Wurfel et al., (2005) "Identification of High and Low Responders to Lipopolysaccharide in Normal Subjects: An Unbiased Approach to Identify Modulators of Innate Immunity" The Journal of Immunology, (175):2570-2578.

\* cited by examiner

DIAGNOSTIC FOR SEPSIS

CROSS-REFERENCE TO RELATED APPLICATION

This application is a continuation of U.S. application Ser. No. 15/124,333, now abandoned, which was the national phase under 35 U.S.C. 371 of the prior PCT application no. PCT/CA2015/000160, which has the International Filing Date of Mar. 13, 2015, which designates the United States of America, and which claims priority to U.S. provisional patent application No. 61/953,458 filed on Mar. 14, 2014 e, the entire contents of which are incorporated by reference herein.

FIELD OF THE INVENTION

The present invention relates to the field of diagnostics and, in particular, to a unique set of DNA sequences that in combination enable the early diagnosis of sepsis, and the prediction of severe sepsis and/or organ failure.

BACKGROUND OF THE INVENTION

Sepsis continues to be the major infection-related cause of death globally, leading to an estimated 8.5% of deaths (5 million) annually [Angus D, et al. Critical Care Medicine 2001; 29(7): 1303-10; Kumar G, Kumar N, Taneja A, et al. Chest 2011; 140:1223-31]. Despite advances in modern medicine including new antibiotics and vaccines, early recognition and best practice treatments, and efficient well-equipped intensive care units [Angus D et al], the high rate of mortality, ~30%, has remained little changed for decades [Daniels R. J Antimicrobial Chemotherapy 2011; 66(Suppl 2): ii11-ii23].

Bacterial endotoxins (including LPS) are potent inducers of inflammation and have been suggested as triggers for sepsis, as the cause of an early life-threatening cytokine storm and septic shock [Opal S M. Contributions to Nephrology 2010; 167: 14-24; Salomao R, et al. Shock 2012; 38:227-42]. In contrast, LPS can also generate an opposite effect known as endotoxin tolerance, defined as the severely reduced capacity of the cell to respond to LPS and other bacterial products during a second exposure to the stimulus [Otto G P, et al. Critical Care 2011; 15:R183]. It is important to note that endotoxin tolerance, also termed cellular reprogramming since it can be induced by other microbial molecules, is not an anti-inflammatory state of cells but rather a reprogramming of cells so they are no longer able of responding to multiple microbial signatures, including endotoxin.

It has been proposed that endotoxin tolerance may be associated with the immunosuppressive state that has been primarily observed during late-stage severe sepsis [Otto G P, et al. 2011; Cavaillon J, et al. J Endotoxin Res 2005; 11(5): 311-20; Cavaillon J, Adib-Conquy M. Critical Care Medicine 2006; 10:233], However, this relationship remains poorly characterized, in part due to the limitations of the ex vivo cytokine assays employed to date. Despite these observations, the clinical dogma is to identify and treat sepsis, especially in its early stages, as an excessive inflammatory response. However, the unique immunosuppressive state characteristic of sepsis is inherently linked to the prognosis of this disease. Indeed, understanding the relative balance between excessive inflammation and immunosuppression, and especially at what time each develops in the clinical course of disease, is an important step towards improving sepsis outcomes.

Biomarkers for the diagnosis of sepsis have been proposed in U.S. Pat. No. 7,767,395; U.S. Patent Application Publication No. 2011/0312521; U.S. Patent Application Publication No. 2011/0076685; International Patent Application Publication No. WO 2014/209238, and International Patent Application Publication No. WO 2013/152047.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates generally to a diagnostic for early severe sepsis. In one aspect, the invention relates to a method for diagnosing sepsis in a subject, comprising determining in a biological sample obtained from the subject a level of expression for each of a plurality of Endotoxin Tolerance Signature genes to provide a sample gene signature, and comparing the sample gene signature with a reference gene signature, wherein the reference gene signature represents a standard level of expression of each of the plurality of genes; wherein a difference between the sample gene signature and the reference gene signature indicates that the subject has sepsis.

In another aspect, the invention relates to a method for identifying a subject at risk of developing severe sepsis, comprising determining in a biological sample obtained from the subject a level of expression for each of a plurality of Endotoxin Tolerance Signature genes to provide a sample gene signature, and comparing the sample gene signature with a reference gene signature, wherein the reference gene signature represents a standard level of expression of each of the plurality of genes; wherein a difference between the sample gene signature and the reference gene signature indicates that the subject is at risk of developing severe sepsis.

In another aspect, the invention relates to a method for identifying a subject at risk of organ failure, comprising determining in a biological sample obtained from the subject a level of expression for each of a plurality of Endotoxin Tolerance Signature genes to provide a sample gene signature, and comparing the sample gene signature with a reference gene signature, wherein the reference gene signature represents a standard level of expression of each of the plurality of genes; wherein a difference between the sample gene signature and the reference gene signature indicates that the subject is at risk of organ failure.

In certain embodiments, the plurality of genes is selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1. CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158. TREM1, TSPAN4, UPP1 and VCAN.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDL1M7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a method for diagnosing endotoxin tolerance in a subject, the method comprising: a) determining in a biological sample obtained from the subject a level of expression for each of a plurality of genes selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN to provide a sample gene signature, and b) comparing the sample gene signature with a reference gene signature, wherein the reference gene signature represents a standard level of expression of each of the plurality of genes; wherein a difference between the sample gene signature and the reference gene signature indicates that the subject has endotoxin tolerance.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a method for treating sepsis comprising administering an effective amount of one or more antibiotics to a subject who has been diagnosed as having sepsis by the method described above.

In another aspect, the invention relates to a method for treating sepsis in a subject, the method comprising: a) determining whether the subject has sepsis or is at risk of developing sepsis by: (i) determining in a biological sample obtained from the subject a level of expression for each of a plurality of genes selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, REIN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN to provide a sample gene signature, and (ii) comparing the sample gene signature with a reference gene signature, wherein the reference gene signature represents a standard level of expression of each of the plurality of genes, and wherein a difference between the sample gene signature and the reference gene signature indicates that the subject has sepsis or is at risk of developing sepsis, and b) if the subject has sepsis or is at risk of developing sepsis, administering to the subject an effective amount of one or more antibiotics.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, REIN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a method for decreasing the risk of organ failure in a subject comprising administering an effective amount of one or more antibiotics to a subject who has been diagnosed as having sepsis or being at risk of developing sepsis by the method described above.

In another aspect, the invention relates to a method for decreasing the risk of organ failure in a subject, the method comprising: a) determining whether the subject is at risk of organ failure by: (i) determining in a biological sample obtained from the subject a level of expression for each of a plurality of genes selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN to provide a sample gene signature, and (ii) comparing the sample gene signature with a reference gene signature, wherein the reference gene signature represents a standard level of expression of each of the plurality of genes, and wherein a difference between the sample gene signature and the reference gene signature indicates that the subject is at risk of organ failure, and b) if the subject is at risk of organ failure, administering to the subject an effective amount of one or more antibiotics.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a method for decreasing the risk of a subject developing severe sepsis comprising administering an effective amount of an agent that counteracts endotoxin tolerance to a subject who has been diagnosed as being at risk of developing severe sepsis by the method described above.

In another aspect, the invention relates to a method for decreasing the risk of organ failure in a subject comprising administering an effective amount of an agent that counteracts endotoxin tolerance to a subject who has been diagnosed as being at risk of organ failure by the method described above.

In another aspect, the invention relates to a method for decreasing the risk of a subject developing severe sepsis or organ failure comprising administering to the subject an effective amount of an agent that counteracts endotoxin tolerance. In certain embodiments, the method may further comprise determining that the subject is at risk of developing severe sepsis or organ failure by: (a) determining in a biological sample obtained from the subject the level of expression of a plurality of genes selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIP A, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN to provide a sample gene signature, and (b) comparing the sample gene signature with a reference gene signature, wherein the reference gene signature represents a standard level of expression of each of the plurality of genes, wherein a difference between the sample gene signature and the reference gene signature indicates that the subject is at risk of developing severe sepsis or organ failure.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2. RAB13, RETN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a method for identifying a candidate agent for the treatment of sepsis, the method comprising: a) contacting an endotoxin tolerant cell with a test agent, b) determining the level of expression for each of a plurality of Endotoxin Tolerance Signature genes in the endotoxin tolerant cell to provide an expression signature, c) comparing the expression signature with a reference expression signature, wherein the reference signature represents the levels of expression of the plurality of genes in a normal cell, and d) selecting the test agent as a candidate agent for treatment of sepsis when the expression signature substantially corresponds with the reference signature.

In certain embodiments, the plurality of genes is selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, REIN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, REIN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDL1M7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a kit for determining a level of expression for each of a plurality of genes selected from ADAM15, ADAMDEC1, ALCAM, ALDH1 A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN in a sample, the kit comprising gene specific reagents, each of the gene specific reagents capable of detecting an expression product of a respective one of the plurality of genes or complement thereof, and instructions for use.

In certain embodiments, the plurality of genes is selected from C19orf59, CCL22, CD14, CD300LF, CYP1B1, DHRS9, FCER1G, FPR1. FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes comprises C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In another aspect, the invention relates to a microarray for detecting expression of a plurality of Endotoxin Tolerance Signature genes in a sample, the microarray comprising a plurality of polynucleotide probes attached to a solid support, each of the polynucleotide probes capable of specifically hybridizing to an expression product of a respective one of the plurality of genes or complement thereof.

In certain embodiments, the plurality of genes are selected from ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLM7, PLAUR, PLD3, PPBP, PROCR, PSTPIP2, PTGES, PTGR1, RAB13, RARRES1, REIN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1 and VCAN.

In certain embodiments, the plurality of genes is selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR. PSTPIP2, RAB13, RETN, RHBDD2, S100A4, S100A9, S100A12, SERPINA1, UPP1, CPVL, CST3, LY86 and PROCR.

In certain embodiments, the plurality of genes comprises C19orf39, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of genes consists of C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

BRIEF DESCRIPTION OF THE FIGURES

These and other features of the invention will become more apparent in the following detailed description in which reference is made to the appended drawings.

DETAILED DESCRIPTION OF THE INVENTION

Figure 1:
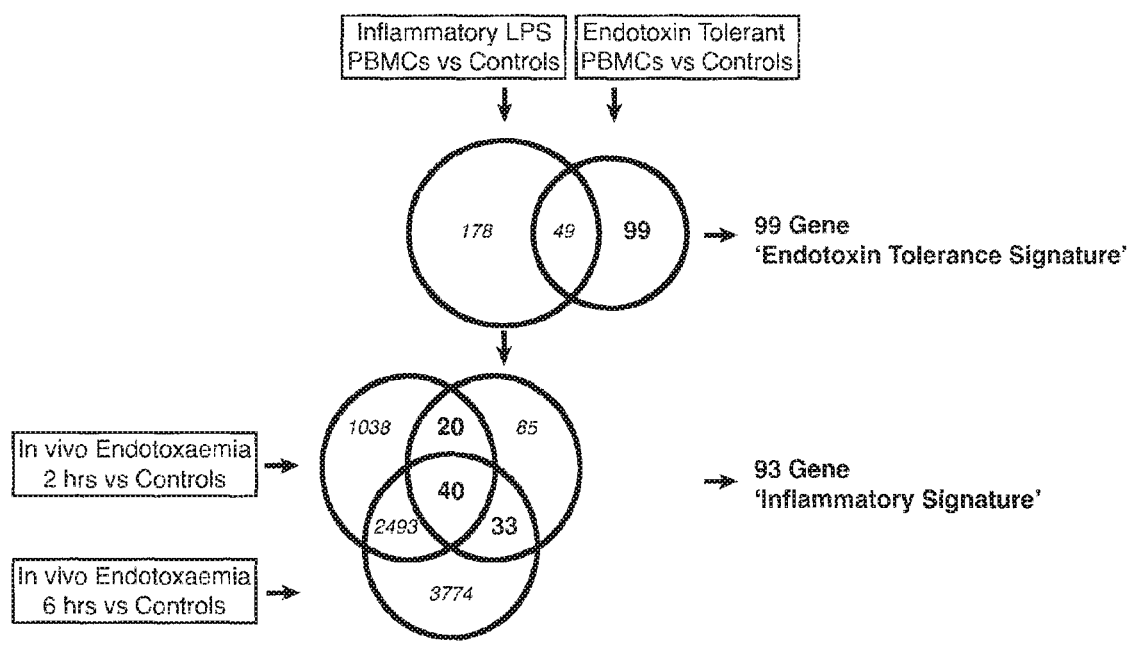
FIG. 1 shows a schematic representation of the method used to define the Endotoxin Tolerance Signature and the Inflammatory Signature. The Endotoxin Tolerance Signature was defined as 99 genes uniquely differentially expressed in endotoxin-tolerant PBMCs, but not inflammatory PBMCs, as compared to controls (fold change>2, p-value<0.05). The Inflammatory Signature was defined as a 93 gene signature by selecting genes that were consistently differentially expressed in an in vivo endotoxaemia dataset.

A unique gene signature characteristic of endotoxin tolerance (an "Endotoxin Tolerance Signature") is identified herein that may be used in the diagnosis of sepsis. The Endotoxin Tolerance Signature is able to differentiate between suspected sepsis patients who either did or did not go on to develop sepsis, and also to predict organ failure.

Certain embodiments of the invention thus relate to methods of diagnosing endotoxin tolerance in a subject, for example a patient known or suspected of having sepsis, using the Endotoxin Tolerance Signature described herein. The presence of endotoxin tolerance is shown to be an indication that a patient has sepsis, and is furthermore an indication that the patient is at risk of developing severe sepsis and/or organ failure. Certain embodiments of the invention relate to methods of diagnosing sepsis in a subject using the Endotoxin Tolerance Signature described herein. In certain embodiments, the sepsis is severe sepsis. Certain embodiments relate to methods of confirming sepsis in a subject suspected of having sepsis a subject using the Endotoxin Tolerance Signature described herein. Some embodiments relate to methods of predicting whether a subject is at risk of developing severe sepsis and/or organ failure using the Endotoxin Tolerance Signature described herein.

As described herein, endotoxin tolerance-mediated immune dysfunction has been determined to be present in a predominant manner upon first presentation and throughout the clinical course of disease. The data provided herein re-defines sepsis as a disease characterized by endotoxin tolerance-mediated immune dysfunction at all stages of clinical disease, and thus identifies endotoxin tolerance as a potential therapeutic target in early and late sepsis.

Certain embodiments of the invention thus relate to methods of treating patients identified as having endotoxin tolerance, for example by using the diagnostic methods described herein, in order to reduce the risk that they will develop sepsis, severe sepsis and/or organ failure. Certain embodiments relate to methods of treating patients having sepsis, including severe sepsis, with an agent that counteracts endotoxin tolerance.

Certain embodiments of the invention relate to methods of identifying candidate agents for treatment of sepsis using the Endotoxin Tolerance Signature described herein.

Certain embodiments relate to a method for diagnosing sepsis in a subject, comprising determining in a biological sample obtained from the subject a level of expression for each of a plurality of Endotoxin Tolerance Signature genes to provide a sample gene signature, and comparing the sample gene signature with a reference gene signature, wherein the reference gene signature represents a standard level of expression of each of the plurality of genes; wherein a difference between the sample gene signature and the reference gene signature indicates that the subject has sepsis.

Certain embodiments relate to a method for identifying a subject at risk of developing severe sepsis, comprising determining in a biological sample obtained from the subject a level of expression for each of a plurality of Endotoxin Tolerance Signature genes to provide a sample gene signature, and comparing the sample gene signature with a reference gene signature, wherein the reference gene signature represents a standard level of expression of each of the plurality of genes; wherein a difference between the sample gene signature and the reference gene signature indicates that the subject is at risk of developing severe sepsis.

Certain embodiments relate to a method for identifying a subject at risk of organ failure, comprising determining in a biological sample obtained from the subject a level of expression for each of a plurality of Endotoxin Tolerance Signature genes to provide a sample gene signature, and comparing the sample gene signature with a reference gene signature, wherein the reference gene signature represents a standard level of expression of each of the plurality of genes; wherein a difference between the sample gene signature and the reference gene signature indicates that the subject is at risk of organ failure.

Definitions

For convenience, the meaning of certain terms and phrases employed in the specification, examples, and appended claims are provided below. The definitions are not meant to be limiting in nature and serve only to facilitate understanding of certain aspects of the invention. Unless defined otherwise, all technical and scientific terms used herein have the same meaning as commonly understood by one of ordinary skill in the art to which this invention belongs.

The term "plurality" as used herein means more than one, for example, two or more, three or more, four or more, and the like.

The term "gene" refers to a nucleic acid sequence that comprises coding sequences necessary for producing a polypeptide or precursor. Control sequences that direct and/or control expression of the coding sequences may also be encompassed by the term "gene" in some instances. The polypeptide or precursor may be encoded by a full length coding sequence or by a portion of the coding sequence. A gene may contain one or more modifications in either the coding or the untranslated regions that could affect the biological activity or the chemical structure of the polypeptide or precursor, the rate of expression, or the manner of expression control. Such modifications include, but are not limited to, mutations, insertions, deletions, and substitutions of one or more nucleotides, including single nucleotide polymorphisms that occur naturally in the population. The gene may constitute an uninterrupted coding sequence or it may include one or more subsequences. The term "gene" as used herein includes variants of the genes identified in Table 1.

The terms "gene expression profile" or "gene signature" refer to a group of genes expressed by a particular cell or tissue type wherein expression of the genes taken together, or the differential expression of such genes, is indicative and/or predictive of a certain condition, such as sepsis.

The term "nucleic acid" as used herein, refers to a molecule comprised of one or more nucleotides, for example, ribonucleotides, deoxyribonucleotides, or both. The term includes monomers and polymers of nucleotides, with the nucleotides being bound together, in the case of the polymers, in sequence, typically via 5' to 3' linkages, although alternative linkages are also contemplated in some embodiments. The nucleotide polymers may be single or double-stranded. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulphur, selenium, phosphorus, and the like.

The term "corresponding to" and grammatical variations thereof as used herein with respect to a nucleic acid sequence indicates that the nucleic acid sequence is identical to all or a portion of a reference nucleic acid sequence. In contradistinction, the term "complementary to" is used herein to indicate that the nucleic acid sequence is identical to all or a portion of the complementary strand of the reference nucleic acid sequence. For illustration, the nucleic acid sequence "TATAC" corresponds to a reference sequence "TATAC" and is complementary to a reference sequence "GTATA." As used herein, "complement thereof" means a nucleic acid that is complementary in nucleotide sequence to a referenced nucleic acid. The complement of an mRNA may be an RNA polynucleotide sequence or a DNA polynucleotide sequence. The complement of a DNA polynucleotide may be an RNA polynucleotide or a DNA polynucleotide.

The term "differential expression" refers to quantitative and/or qualitative differences in the expression of a gene or a protein in diseased tissue or cells versus normal tissue or cells. For example, a differentially expressed gene may have its expression activated or completely inactivated in normal versus disease conditions, or may be up-regulated (over-expressed) or down-regulated (under-expressed) in a disease condition versus a normal condition. Stated another way, a gene or protein is differentially expressed when expression of the gene or protein occurs at a higher or lower level in the diseased tissues or cells of a patient relative to the level of its expression in the normal (disease-free) tissues or cells of the patient and/or control tissues or cells.

The term "biological sample" refers to a sample obtained from an organism (e.g., a human patient) or from components (e.g., cells) of an organism. The sample may be of any relevant biological tissue or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

h is contemplated that any embodiment discussed herein can be implemented with respect to any of the disclosed methods, uses or compositions of the invention, and vice versa.

Sepsis

"Sepsis" generally refers to a clinical response to a suspected or proven infection. Sepsis may be defined, for example, as including two or more of the following symptoms: tachypnea or tachycardia; leukocytosis or leukopenia; and hyperthermia or hypothermia, and may manifest as a complex infectious and immunological disorder. Many other symptoms may or may not occur and have been defined by consensus meetings of physicians (see Bone R C, Balk R A, Cerra F B, et al. Chest 2009; 136(5 Suppl):e28), however none of these symptoms are specific for sepsis. Sepsis may be complicated by organ failure and may require admission to an intensive care ward in which case it is termed "severe sepsis." When a patient, often in the emergency ward, acquires some of the early symptoms associated with sepsis, they are frequently considered to be suspected sepsis patients, which triggers a special hospital protocol for treatment. However, only retrospectively after 24-48 hours when infection is confirmed by microbiological tests or the patient acquires more severe symptoms including failure of one of more organs, are they confirmed to have been "early stage sepsis" patients (see review in Lyle N H, et al., Annals of the New York Academy of Sciences 2014, 1323:101-14).

Endotoxin Tolerance Signature

In one aspect, the invention relates to a plurality of genes regulated during sepsis, the expression profile of which serves to define endotoxin tolerance in a subject. Differences in expression of these genes, either up- or down-regulation depending on the gene in question, when compared to a control defines a gene signature that is indicative of endotoxin tolerance (an "Endotoxin Tolerance Signature"). Non-limiting examples of endotoxin tolerance signature genes (ETSGs) that may be comprised by an Endotoxin Tolerance Signature in accordance with certain embodiments of the invention are provided in Table 1.

The sequences of these genes can readily be obtained by one of skill in the art from publicly available databases, such as the GenBank database maintained by the National Center for Biotechnology (NCBI), for example, by searching using the provided gene symbols. These gene symbols are universally recognized by all databases including HGNC, Entrez Gene, UniProtKB/Swiss-ProU OMIM, GeneLoc, and Ensembl; all aliases are defined by the Gene Cards database. Non-limiting examples of representative gene sequences available from GenBank are provided in Table 1.

TABLE 1

Representative Endotoxin Tolerance Signature genes (ETSGs)

| Gene Symbol | Description | GenBank RefSeq # | Up (+) or Down (−) Regulation |
|---|---|---|---|
| ADAM15 | ADAM metallopeptidase domain 15 | NP_001248393.1 | − |
| ADAMDEC1 | ADAM-like, decysin 1 | NP_001138743.1 | + |
| ALCAM | Activated leukocyte cell adhesion molecule | NP_001230209.1 | − |
| ALDH1A1 | Aldehyde dehydrogenase 1 family, member A1 | NP_000680.2 | − |
| ANKRD1 | Ankyrin repeat domain 1 (cardiac muscle) | NP_055206.2 | + |
| C19orf59 | Chromosome 19 open reading frame 59 | NP_777578.2 | + |
| CA12 | Carbonic anhydrase XII | NP_001209.1 | + |
| CAMP | Cathelicidin antimicrobial peptide | NP_004336.3 | − |
| CCL1 | Chemokine (C-C motif) ligand 1; SCYA1 | NP_002972.1 | + |
| CCL19 | Chemokine (C-C motif) ligand 19; MIP3β | NP_006265.1 | + |
| CCL22 | Chemokine (C-C motif) ligand 22; MDC | NP_002981.2 | + |
| CCL24 | Chemokine (C-C motif) ligand 24; Eotaxin-2 | NP_002982.2 | + |
| CCL7 | Chemokine (C-C motif) ligand 7 | NP_006264.2 | + |
| CD14 | CD14 molecule | NP_000582.1 | + |
| CD300LF | CD300 molecule-like family member F | NP_001276011.1 | + |
| CD93 | CD93 molecule | NP_036204.2 | + |
| CDK5RAP2 | CDK5 regulatory subunit associated protein 2 | NP_001011649.1 | + |
| CPVL | Carboxypeptidase, Vitellogenic-like | NP_061902.2 | − |
| CST3 | Cystatin C | NP_000090.1 | − |
| CST6 | Cystatin E/M | NP_001314.1 | − |
| CTSK | Cathepsin K | NP_000387.1 | − |
| CXCL10 | Chemokine (C-X-C motif) ligand 10 | NP_001556.2 | − |
| CYP1B1 | Cytochrome P450, family 1, subfamily B, polypeptide 1 | NP_000095.2 | + |
| CYP27B1 | Cytochrome P450, family 27, subfamily B, polypeptide 1 | NP_000776.1 | + |
| DDIT4 | DNA-damage-inducible transcript 4 | NP_061931.1 | + |
| DHRS9 | Dehydrogenase/reductase (SDR family) member 9 | NP_001135742.1 | − |
| DPYSL3 | Dihydropyrimidinase-like 3 | NP_001184223.1 | + |
| EGR2 | Early growth response 2 | NP_000390.2 | + |
| EMR1 | EGF-like module containing, mucin-like, hormone receptor-like 1 | NP_001243181.1 | + |
| EMR3 | EGF-like module containing, mucin-like, hormone receptor-like 3 | NP_001276087.1 | + |
| FBP1 | Fructose-1,6-bisphosphatase 1 | NP_000498.2 | + |
| FCER1G | Fc fragment of IgE, high affinity I, receptor for; gamma polypeptide | NP_004097.1 | + |
| FCER2 | Fc fragment of Ige, low affinity II, receptor for (CD23) | NP_001193948.2 | + |
| FPR1 | Formyl peptide receptor 1 | NP_001180235.1 | + |
| FPR2 | Formyl peptide receptor 2 | NP_001005738.1 | + |
| GK | Glycerol kinase | NP_000158.1 | + |

TABLE 1-continued

Representative Endotoxin Tolerance Signature genes (ETSGs)

| Gene Symbol | Description | GenBank RefSeq # | Up (+) or Down (−) Regulation |
|---|---|---|---|
| GPNMB | Glycoprotein (transmembrane) NMB | NP_001005340.1 | − |
| GPR137B | G protein-coupled receptor 137B | NP_003263.1 | + |
| HBEGF | Heparin-binding EGF-like growth factor | NP_001936.1 | + |
| HIST1H1C | Histone cluster 1, H1C | NP_005310.1 | + |
| HIST2H2AA3 | Histone cluster 2, H2AA3 | NP_001035807.1 | + |
| HIST2H2AC | Histone cluster 2, H2AC | NP_003508.1 | + |
| HK2 | Hexokinase 2 | NP_000180.2 | + |
| HK3 | Hexokinase 3 (white cell) | NP_002106.2 | + |
| HPSE | Heparanase | NP_001092010.1 | + |
| HSD11B1 | Hydroxysteroid (11-beta) dehydrogenase 1 | NP_001193670.1 | + |
| HTRA1 | HTRA serine peptidase 1 | NP_002766.1 | − |
| IL18BP | Interleukin 18 binding protein | NP_001034748.1 | − |
| IL3RA | Interleukin 3 receptor, alpha (low affinity) | NP_001254642.1 | + |
| ITGB8 | Integrin, beta 8 | NP_002205.1 | + |
| KIAA1199 | KIAA1199 | NP_001280227.1 | + |
| LILRA3 | Leukocyte immunoglobulin-like receptor, subfamily A (without TM domain), member 3 | NP_001166125.1 | + |
| LILRA5 | Leukocyte immunoglobulin-like receptor, subfamily A (with TM domain), member 5 | NP_067073.1 | + |
| LIPA | Lipase A, lysosomal acid, cholesterol esterase | NP_000226.2 | − |
| LY86 | Lymphocyte antigen 86 | NP_004262.1 | − |
| MARCO | Macrophage receptor with collagenous structure | NP_006761.1 | + |
| MGST1 | Microsomal glutathione S-transferase 1 | NP_001247440.1 | + |
| MMP7 | Matrix metallopeptidase 7 (matrilysin, uterine) | NP_002414.1 | + |
| MT1F | Metallothionein 1F | NP_001288201.1 | + |
| MT1G | Metallothionein 1G | NP_001288196.1 | + |
| MT1H | Metallothionein 1H | NP_005942.1 | + |
| MT1M | Metallothionein 1M | NP_789846.1 | + |
| MT1X | Metallothionein 1X | NP_005943.1 | + |
| MXD1 | MAX dimerization protein 1 | NP_001189442.1 | + |
| MYADM | Myeloid-associated differentiation marker | NP_001018654.1 | + |
| NEFH | Neurofilament, heavy polypeptide | NP_066554.2 | + |
| NQO1 | NAD(P)H dehydrogenase, Quinone 1 | NP_000894.1 | − |
| NRIP3 | Nuclear receptor interacting protein 3 | NP_065696.1 | + |
| OLIG2 | Oligodendrocyte lineage transcription factor 2 | NP_005797.1 | + |
| PANX2 | Pannexin 2 | NP_001153772.1 | + |
| PAPLN | Papilin, proteoglycan-like sulfated glycoprotein | NP_775733.3 | + |
| PDLIM7 | PDZ and LIM domain 7 (enigma) | NP_005442.2 | + |
| PLAUR | Plasminogen activator, Urokinase receptor | NP_001005376.1 | + |
| PLD3 | Phospholipase D family, member 3 | NP_001026866.1 | − |
| PPBP | Pro-platelet basic protein (chemokine (C-X-C motif) ligand 7) | NP_002695.1 | + |
| PROCR | Protein C receptor, endothelial | NP_006395.2 | + |
| PSTPIP2 | Proline-serine-threonine phosphatase interacting protein 2 | NP_077748.3 | − |
| PTGES | Prostaglandin E synthase | NP_004869.1 | + |
| PTGR1 | Prostaglandin reductase 1 | NP_001139580.1 | + |
| RAB13 | RAB13, member RAS oncogene family | NP_001258967.1 | + |
| RARRES1 | Retinoic acid receptor responder (Tazarotene induced) 1 | NP_002879.2 | − |
| RETN | Resistin | NP_001180303.1 | + |
| RHBDD2 | Rhomboid domain containing 2 | NP_001035546.1 | + |
| RNASE1 | Ribonuclease, RNAse A family, 1 (pancreatic) | NP_002924.1 | − |
| S100A12 | S100 calcium binding protein A12 | NP_005612.1 | + |
| S100A4 | S100 calcium binding protein A4 | NP_002952.1 | − |
| S100A8 | S100 calcium binding protein A8 | NP_002955.2 | + |
| S100A9 | S100 calcium binding protein A9 | NP_002956.1 | + |
| SERPINA1 | Serpin peptidase inhibitor, Clade A (α-1 anti-proteinase, anti-trypsin), member 1 | NP_000286.3 | + |
| SERPINB7 | Serpin peptidase inhibitor, Clade B (ovalbumin), member 7 | NP_001035237.1 | + |
| SLC16A10 | Solute carrier family 16, member 10 (aromatic amino acid transporter) | NP_061063.2 | + |
| SLC7A11 | Solute carrier family 7 (anionic amino acid transporter light chain, xc-system), member 11 | NP_055146.1 | + |
| TGM2 | Transglutaminase 2 | NP_004604.2 | + |
| TLR7 | Toll-like receptor 7 | NP_057646.1 | − |
| TMEM158 | Transmembrane protein 158 (gene/pseudogene) | NP_056259.2 | + |
| TREM1 | Triggering receptor expressed on myeloid cells 1 | NP_001229518.1 | + |
| TSPAN4 | Tetraspanin 4 | NP_001020405.1 | − |
| UPP1 | Uridine phosphorylase 1 | NP_001274355.1 | + |
| VCAN | Versican | NP_001119808.1 | + |

An Endotoxin Tolerance Signature may comprise all endotoxin tolerance signature genes (ETSGs) shown in Table 1, or it may comprise a subset of these genes. In certain embodiments, the Endotoxin Tolerance Signature may comprise as few as two ETSGs and up to 99 of the ETSGs shown in Table 1. In some embodiments, the Endotoxin Tolerance Signature comprises at least three, at least four, at least five, at least six, at least seven, at least eight, at least nine, at least ten, at least eleven, at least twelve, at least thirteen, at least fourteen, at least fifteen of the ETSGs of Table 1. In some embodiments, the Endotoxin Tolerance Signature comprises 15 or more ETSGs, for example, 20 or more, 25 or more or 30 or more ETSGs. In some embodiments, the Endotoxin Tolerance Signature comprises about 31 ETSGs of Table 1. In some embodiments, the Endotoxin Tolerance Signature comprises about 35, 40, 45, 50, 55, 60, 65, 70, 75, 80, 85, 90, 95, or 99 ETSGs.

In certain embodiments, the Endotoxin Tolerance Signature comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1.

In certain embodiments, the Endotoxin Tolerance Signature comprises at least 2, 3, 4, 5, 6, 7, 8, 9, 10, 11, 12, 13, 14, 15 ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In some embodiments, the Endotoxin Tolerance Signature comprises at least 15, at least 20, at least 25 or at least 30 ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the Endotoxin Tolerance Signature comprises 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR, and may optionally comprise one or more other ETSGs from Table 1.

In some embodiments, the Endotoxin Tolerance Signature comprises the ETSGs: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR, and may optionally comprise one or more other ETSGs from Table 1.

The change in expression of an ETSG may be defined by an expression change direction, which indicates whether the gene is up- or down-regulated in a subject with endotoxin tolerance when compared to expression of the ETSG in a control (or reference) sample. With reference to the ETSGs shown in Table 1 for example, a subject with endotoxin tolerance would show an upregulation of one or more of ADAMDEC1, ANKRD1, C19orf59, CA12, CCL1, CCL19, CCL22, CCL24, CCL7, CD14, CD300LF, CD93, CDK5RAP2, CYP1B1, CYP27B1, DDIT4, DPYSL3, EGR2, EMR1, EMR3, FBP1, FCER1G, FCER2, FPR1, FPR2, GK, GPR137B, HBEGF, HIST1H1C, HIST2H2AA3, HIST2H2AC, HK2, HK3, HPSE, HSD11B1, IL3RA, ITGB8, KIAA1199, LILRA3, LILRA5, MARCO, MGST1, MMP7, MT1F, MT1G, MT1H, MT1M, MT1X, MXD1, MYADM, NEFH, NRIP3, OLIG2, PANX2, PAPLN, PDLIM7, PLAUR, PPBP, PROCR, PTGES, PTGR1, RAB13, RETN, RHBDD2, S100A12, S100A8, S100A9, SERPINA1, SERPINB7, SLC16A10, SLC7A11, TGM2, TMEM158, TREM1, UPP1 or VCAN, and a down-regulation of one or more of ADAM15, ALCAM, ALDH1A1, CAMP, CPVL, CST3, CST6, CTSK, CXCL10, DHRS9, GPNMB, HTRA1, IL18BP, LIPA, LY86, NQO1, PLD3, PSTPIP2, RARRES1, RNASE1, S100A4, TLR7 or TSPAN4.

The change in expression of an ETSG may be optionally further defined by a minimum fold change in expression level over control. In certain embodiments, up- or down-regulation of a given ETSG may be defined as an at least 1.5-fold change in the level of expression of the gene when compared to a control. In some embodiments, up- or down-regulation of a given ETSG may be defined as a 2-fold or greater change in the level of expression of the gene when compared to a control. A control (or standard or reference) level of expression may be, for example, the level of expression of the ETSG in a sample from a healthy subject, or the level of expression of the ETSG in a non-endotoxin tolerant cell.

Methods

Diagnostic Methods

Certain embodiments of the invention relate to diagnostic methods that use the Endotoxin Tolerance Signature to determine whether a subject having or suspected of having sepsis has endotoxin tolerance and is, therefore, at risk of developing one or more of sepsis, severe sepsis and/or organ failure.

In certain embodiments, the subject is suspected of having sepsis and the method identifies the patient as having sepsis. In some embodiments, the subject is suspected of having sepsis and the method identifies the subject as being at risk of developing severe sepsis and/or organ failure. In certain embodiments, the subject is suspected of having sepsis and the method identifies the patient as having severe sepsis.

Generally, the diagnostic methods comprise detecting the expression of the genes comprised by the Endotoxin Tolerance Signature in a biological sample obtained from a test subject. Differences in expression of these genes when compared to a control are determined. A difference in expression of at least two of these genes in the defined expression change direction is indicative that the subject has, or is at risk of developing, one or more of sepsis, severe sepsis and/or organ failure.

In certain embodiments, a difference in expression of three or more, four or more, five or more, six or more, seven or more, eight or more, nine or more, ten or more, eleven or more, twelve or more, thirteen or more, fourteen or more, or fifteen or more of the ETSGs in the Endotoxin Tolerance Signature when compared to a control sample is indicative that the subject has, or is at risk of developing, one or more of sepsis, severe sepsis and/or organ failure. In some embodiments, a difference in expression of at least 15, at least 20, at least 25 or at least 30 of the ETSGs in the Endotoxin Tolerance Signature when compared to a control sample is indicative that the subject has, or is at risk of developing, one or more of sepsis, severe sepsis and/or organ failure. In some embodiments, a difference in expression of about 31 of the ETSGs in the Endotoxin Tolerance Signature when compared to a control sample is indicative that the subject has, or is at risk of developing, one or more of sepsis, severe sepsis and/or organ failure.

In alternative embodiments, a difference in expression of at least 20% of the ETSGs in the Endotoxin Tolerance Signature when compared to a control sample is indicative that the subject has, or is at risk of developing, one or more of sepsis, severe sepsis and/or organ failure. In some embodiments, a difference in expression of 20% or more, 30% or more, 40% or more, 50% or more, 60% or more, 70% or more, 80% or more, or 90% or more of the ETSGs in the Endotoxin Tolerance Signature when compared to a control sample is indicative that the subject has, or is at risk of developing, one or more of sepsis, severe sepsis and/or organ failure. In some embodiments, a difference in expression of at least 35% of the ETSGs in the Endotoxin Tolerance Signature when compared to a control sample is indicative that the subject has, or is at risk of developing, one or more of sepsis, severe sepsis and/or organ failure.

In some embodiments, a difference in expression of each of the ETSGs in an Endotoxin Tolerance Signature when compared to a control sample is indicative that the subject has, or is at risk of developing, one or more of sepsis, severe sepsis and/or organ failure, wherein the Endotoxin Tolerance Signature may comprise between two and about 99 ETSGs, for example, between about 3, 4, 5, 6, 7, 8, 9, 10, 11, 12, 13, 14, 15, 20, 25 or 30 and about 99 ETSGs.

In certain embodiments, a difference in expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1 when compared to a control sample is indicative that the subject has, or is at risk of developing, one or more of sepsis, severe sepsis and/or organ failure.

In certain embodiments, a difference in expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the following ETSGs when compared to a control sample is indicative that the subject has, or is at risk of developing, one or more of sepsis, severe sepsis and/or organ failure: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

The biological sample may comprise, for example, blood, plasma, serum, tissue, amniotic fluid, saliva, urine, stool, bronchoalveolar lavage fluid, cerebrospinal fluid, or cells (such as skin cells) or cellular extracts.

The expression of the ETSGs comprised by the Endotoxin Tolerance Signature may be determined by detection of an expression product of each gene. The expression product may be, for example, RNA. cDNA prepared from RNA, or protein. When the expression product is RNA or cDNA, the entire sequence of the gene may be detected, or any definitive portion of the gene, for example, a sequence of 10 nucleotides or more, may be detected.

Methods of detecting and quantifying expression of genes are well-known in the art (see, for example, *Current Protocols in Molecular Biology,* 1987 & updates, Ausubel et al. (ed.), Wiley & Sons, New York, NY) and include the use of detectably labelled polynucleotide probes, antibodies, aptamers, and the like.

In certain embodiments, one or more of polymerase chain reaction (PCR), reverse transcriptase-(RT) PCR, Q-beta replicase amplification, ligase chain reaction, nucleic acid sequence amplification, signal amplification (Ampliprobe), light cycling, differential display. Northern analysis, hybridization, microarrays, RNA-Seq, nucleic acid sequencing, MassArray analysis, and MALDI-TOF mass spectrometry may be employed in determining expression of the ETSGs.

In certain embodiments, the diagnostic methods employ detectably labelled polynucleotides for detecting expression of the ETSGs. The methods may further comprise one or more of isolation of nucleic acids from the sample, purification of the nucleic acids, reverse transcription of RNA, and/or nucleic acid amplification. In some embodiments, the polynucleotide probes used to determine expression of the ETSGs may be immobilized on a solid support, for example, as an array or microarray allowing for more rapid processing of the sample. Methods of preparing arrays and microarrays are well known in the art. In addition, a number of standard microarrays are available commercially that include probes for detecting some of the genes identified herein as ETSGs and thus may be suitable for use in the disclosed diagnostic methods. For example, Affymetrix U133 GeneChip™ arrays (Affymetrix, Inc., Santa Clara, CA), Agilent Technologies genomic cDNA microarrays (Santa Clara, CA), and arrays available from Illumina, Inc. (San Diego, CA). These arrays have probe sets for the whole human genome immobilized on a chip, and can be used to determine up- and down-regulation of genes in test samples. Custom-made arrays and microarrays for detecting pre-selected genes are also available commercially from a number of companies. Instruments and reagents for performing gene expression analysis are commercially available (for example, the Affymetrix GeneChip™ System). The expression data obtained from the analysis may then be input into an appropriate database for further analysis if necessary or desired.

In some embodiments, the differentially expressed genes can be detected, after conversion to cDNAs by the use of Matrix-assisted laser desorption/ionization—time of flight (MALDI-TOF) mass spectrometry using, for example the Sequenom MassARRAY® system (see, for example, Kricka L J. Clin Chem 1999; 45:453-458).

The expression of certain genes known as "reference genes," "control genes" or "housekeeping genes" may also be determined in the sample as a means of ensuring the veracity of the expression profile. Reference genes are genes that are consistently expressed in many tissue types, including cancerous and normal tissues, and thus are useful to normalize gene expression profiles. Determining the expression of reference genes in parallel with the genes in the Endotoxin Tolerance Signature provides further assurance that the techniques used for determination of the gene expression profile are working properly. Appropriate reference genes (also referred to herein as control genes and housekeeping genes) can be readily selected by the skilled person.

The expression levels determined for the ETSGs of the Endotoxin Tolerance Signature are compared to a suitable reference or control, which may be for example expression levels of the ETSGs in a biological sample from a healthy individual or expression levels of the ETSGs in a non-endotoxin tolerant cell. The comparison may include, for example, a visual inspection and/or an arithmetic or statistical comparison of measurements and may take into account expression of any reference genes. Suitable methods of comparison to determine differences in expression levels of genes are well known in the art.

In certain embodiments, the diagnostic methods may be used as confirmatory diagnostics to standard sepsis diagnostic procedures. In some embodiments, the diagnostic methods may be used as a stand-alone diagnostic.

In certain embodiments, the diagnostic methods may be used to confirm sepsis in a subject suspected of having sepsis. The subject may have already undergone one or more assessments to determine whether they meet the standard diagnostic criteria for sepsis, for example, microbial culture analysis, measurement of blood pressure, white blood cell count, measurement of temperature, measurement of respiratory rate, and/or measurement of heart rate. In certain embodiments, the diagnostic method may be used to confirm sepsis in a patient having been diagnosed as having sepsis by standard diagnostic criteria. In certain embodiments, the diagnostic method may be used to diagnose a patient with sepsis as having severe sepsis and/or being at risk of organ failure.

In certain embodiments, determining the level of expression of ETSGs in a biological sample comprises detecting the presence in the biological sample of a plurality of mRNAs encoded by a plurality of ETSGs. In some embodiments, detecting the presence in the sample of mRNAs encoded by the ETSGs comprises performing a reverse transcription reaction using mRNAs obtained from the biological sample to generate cDNA products, and contacting the cDNA products with nucleic acid probes that are capable of hybridizing to cDNAs that comprise nucleotide sequences complementary to mRNAs encoded by the ETSGs.

In some embodiments, the methods comprise contacting cDNA products generated by a reverse transcription reaction using mRNAs obtained from a biological sample with a microarray comprising nucleic acid probes capable of hybridizing to cDNAs that comprise nucleotide sequences complementary to mRNAs encoded by a plurality of ETSGs.

Methods of Treatment

In certain embodiments, the invention relates to methods of treating patients identified as having endotoxin tolerance, for example by using the diagnostic methods described herein, in order to reduce the risk that they will develop sepsis, severe sepsis and/or organ failure. In certain embodiments, early identification of the immunological state of sepsis patients by the methods described herein helps to guide selection of an appropriate therapy.

In certain embodiments, when a patient is identified as having endotoxin tolerance and being at risk of developing sepsis, severe sepsis and/or organ failure, the method of treatment comprises administering a therapeutically effective dose of at least one antibiotic that is indicated for the treatment of severe sepsis to the patient.

Examples of suitable antibiotics for treating severe sepsis include, but are not limited to, glycopeptides (such as vancomycin, oritavancin or televancin) cephalosporins (such as ceftriaxone, cefotaxime, or cefepime), beta-lactams/beta-lactamase inhibitors (such as piperacillin-tazobactam, ticarcillin-clavulanate), carbapenems (such as imipenem or meropenem), quinolones and fluoroquinolones (such as ciprofloxacin, moxifloxacin or levofloxacin), aminoglycosides (such as gentamicin, tobramycin or amikacin), macrolides (such as azithromycin, clarithromycin or erythromycin) and monobactams (such as aztreonam), and various combinations thereof. Typically combinations comprise antibiotics from different classes.

As demonstrated herein, sepsis may be defined as a disease characterized by endotoxin tolerance-mediated immune dysfunction. Thus counteracting endotoxin tolerance in sepsis patients is a potential therapeutic approach to prevent or decrease the likelihood of the patient developing severe sepsis and/or organ failure. Accordingly, in some embodiments, the invention relates to methods of treating a patient with sepsis that comprise administering to the patient an agent that counteracts endotoxin tolerance. In some embodiments, the invention relates to a method of preventing or decreasing the risk of a patient developing severe sepsis and/or organ failure comprising administering to the patient an agent that counteracts endotoxin tolerance. In certain embodiments, patients are identified as being at risk of developing sepsis, severe sepsis and/or organ failure by the diagnostic methods described herein.

The agent that counteracts endotoxin tolerance may be, for example, an immunotherapy. In some embodiments, the agent that counteracts endotoxin tolerance comprises immune cells. Other examples of agents that counteract endotoxin tolerance include, but are not limited to, interferon-gamma, CpG oligonucleotides alone or in combination with IL-10, anti-CD40 antibodies, inhibitors of STAT3, inhibitors of STAT6, inhibitors of p50, inhibitors of NFκB, inhibitors of IKKβ, imidazoquinolines and zoledronic acid.

Endotoxin tolerance may result in macrophages being "locked" into an M2 state. In certain embodiments, the agent that counteracts endotoxin tolerance is capable of altering macrophage phenotype from M2 to M1, or M2 to M0 (which represents uncommitted macrophages).

In some embodiments, the invention relates to methods of treating a patient with sepsis that comprise administering to the patient an agent that alters macrophage phenotype from M2 to M1. In some embodiments, the invention relates to a method of preventing or decreasing the risk of a patient developing severe sepsis and/or organ failure comprising administering to the patient an agent that alters macrophage phenotype from M2 to M1. In certain embodiments, patients are identified as being at risk of developing sepsis, severe sepsis and/or organ failure by the diagnostic methods described herein.

In certain embodiments, the agent capable of altering macrophage phenotype from M2 to M1 is selected from an immunotherapy, immune cells, interferon-gamma, CpG oligonucleotides alone or in combination with IL-10, anti-CD40 antibodies, inhibitors of STAT3, inhibitors of STAT6, inhibitors of p50, inhibitors of NFκB, inhibitors of IKKβ, imidazoquinolines and zoledronic acid.

Certain embodiments of the invention relate to a method for decreasing the risk of a subject developing severe sepsis comprising administering an effective amount of an agent that counteracts endotoxin tolerance to a subject in need thereof. In some embodiments, the subject has been diagnosed as being at risk for developing severe sepsis by a method disclosed herein.

Certain embodiments of the invention relate to a method for decreasing the risk of organ failure in a subject comprising administering an effective amount of an agent that counteracts endotoxin tolerance to a subject in need thereof. In some embodiment, the subject has been diagnosed as being at risk of organ failure by a method disclosed herein.

Certain embodiments of the invention relate to a method for treating sepsis, comprising administering an effective amount of an agent that counteracts endotoxin tolerance to a subject in need thereof. In some embodiments, the subject has been diagnosed as having sepsis by a method disclosed herein.

In one embodiment, the agent that counteracts endotoxin tolerance and finds use in methods disclosed herein may be an immunotherapy. In one embodiment, the agent that counteracts endotoxin tolerance and finds use in methods disclosed herein comprises immune cells. In one embodiment, the immune cell is a syngeneic immune cell, for example, the cell may be from the subject to whom the immune cell is being administered. In another embodiment, the immune cell is an allogeneic immune cell, that is, from an individual other than the subject to whom the immune cell is being administered.

In one embodiment, the agent that counteracts endotoxin tolerance and finds use in methods disclosed herein is interferon gamma. In one embodiment, the agent that counteracts endotoxin tolerance and finds use in methods disclosed herein is a CpG-oligonucleotide (ODN). In one embodiment, the agent that counteracts endotoxin tolerance and finds use in methods disclosed herein is a combination of a CpG ODN and interleukin-10 (IL-10). In one embodiment, the agent that counteracts endotoxin tolerance and finds use in methods disclosed herein is an anti-CD40 antibody. In one embodiment, the agent that counteracts endotoxin tolerance and finds use in methods disclosed herein is an inhibitor of STAT3. In one embodiment, the agent that counteracts endotoxin tolerance and finds use in methods disclosed herein is an inhibitor of STAT-6. In one embodiment, the agent that counteracts endotoxin tolerance and finds use in methods disclosed herein is an inhibitor of p50. In one embodiment, the agent that counteracts endotoxin tolerance and finds use in methods disclosed herein is an inhibitor of NFκB. In one embodiment, the agent that counteracts endotoxin tolerance and finds use in methods disclosed herein is an inhibitor of IKκ3. In one embodiment, the agent that counteracts endotoxin tolerance and finds use in methods disclosed herein is an imidazoouinoline. In one embodiment, the agent that counteracts endotoxin tolerance and finds use in methods disclosed herein is zoledronic acid.

Methods of Screening

Certain embodiments of the invention relate to methods for identifying a candidate agent for the treatment of sepsis by evaluating the effect of a test agent on the expression of the ETSGs comprised by an Endotoxin Tolerance Signature. The ability of the test compound to affect expression of the ETSGs may be assessed for example by contacting a cell in vitro with the test compound, determining the expression of the ETSGs in the cell and comparing the expression of the ETSGs in the cell with the level of expression of the same ETSGs in a control cell.

Expression of the ETSGs may be assessed by various methods known in the art as described herein and elsewhere.

In certain embodiments, the test cell may be an endotoxin tolerant cell and the control cell may be a non-endotoxin tolerant (normal) cell. In accordance with this embodiment, if the pattern of expression (or gene signature) of the cell treated with the test agent substantially corresponds to the pattern of expression (or gene signature) of the control cell, this indicates that the test agent is a candidate agent for the treatment of sepsis. By "substantially corresponds" in this context, it is meant that expression of those ETSG that are upregulated in exotoxin tolerant cells is decreased and expression of those ETSGs that are downregulated in exotoxin tolerant cells is increased.

In some embodiments, the level of expression of at least one of the ETSGs in the treated cell is within a predetermined margin of the level of expression of the same ETSG in the control cell. For example, within about ±0.25%, within about ±20%, within about ±15%, or within about ±10% of the level of expression of the same ETSG in the control cell.

In some embodiments, the method may further comprise contacting the cell with an endotoxin for a sufficient time to induce endotoxin tolerance in the cell prior to contacting the cell with the test agent. The endotoxin may be, for example, a bacterial lipopolysaccharide (LPS) or lipoteichoic acid or a combination thereof. The LPS or lipoteichoic acid may be in an isolated form, or may be provided by contacting the cell with a bacterium that naturally contains the LPS and/or lipoteichoic acid. The amount of time required to induce endotoxin tolerance can be readily determined by the skilled person. More than one treatment with endotoxin may be required to induce endotoxin tolerance. In general, a time between about 12 and about 24 hours may be used, for example, about 14, about 16, about 18 or about 20 horns, and between one and three treatments with endotoxin. When multiple treatments are used, the endotoxin used in each treatment may be the same or different.

In some embodiments the method of screening may include assessing the endotoxin tolerant cell for restoration of the ability to react to endotoxin, thus indicating that the test agent is capable of breaking tolerance in the cell. In some embodiments, the method of screening further comprises contacting a second cell with an agent known to counteract endotoxin tolerance, such as interferon-gamma, a CpG-oligonucleotide (with or without IL-10), an anti-CD40 antibody, an inhibitor of STAT3, an inhibitor of STATE, an inhibitor of p50, an inhibitor of NFκB, an inhibitor of IKKIβ, an imidazoquinoline or zoledronic acid, and determining the expression of the same ETSGs in the second cell.

In certain embodiments, the method may further comprise assaying the test agent for the ability to alter macrophage phenotype from M2 to M1.

Kits and Microarrays

Certain embodiments of the invention relate to kits useful for detecting ETSGs as identified herein. Accordingly, the kit will comprise one or more reagents for determining expression of a plurality, for example two or more. ETSGs. Typically, the kit will comprise a collection of reagents, for example, two or more, that are used together to perform a diagnostic method, or one or more steps of a diagnostic method, as described herein, and which are provided together, usually within a common packaging.

The one or more reagents for determining expression of an ETSG may comprise a gene specific probe that is capable of detecting an expression product of the ETSG (nucleic acid or protein) or the complement of a nucleic acid expression product. Polynucleotide primers for reverse transcription of mRNA encoded by the ETSG, and/or for amplification of a nucleic acid sequence from the ETSG or from cDNA prepared from the ETSG encoded mRNA may also be provided in the kit.

In certain embodiments, the kit comprises gene specific probes for a plurality of ETSGs are selected from the ETSGs listed in Table 1. In some embodiments, the plurality of ETSGs comprise C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, a kit comprises gene specific probes for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1.

In certain embodiments, the gene specific probes of a kit that are specific for ETSGs comprise probes for ETSGs selected from Table 1.

In certain embodiments, the gene specific probes of a kit that are specific for ETSGs consist of probes for ETSGs selected from Table 1.

In certain embodiments, the gene specific probes of a kit that are specific for ETSGs consists of probes for all the ETSGs in Table 1.

In certain embodiments, the gene specific probes of a kit that are specific for ETSGs comprise probes for ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the gene specific probes of a kit that are specific for ETSGs consist of probes for ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the gene specific probes of a kit that are specific for ETSGs consist of probes for each of the following: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, a kit comprises gene specific probes for 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the following ETSGs: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the kit may comprise or consist of a microarray that comprises a plurality of ETSG specific polynucleotide probes immobilized onto a solid support. The microarray may further comprise control polynucleotide probes specific for control sequences, such as housekeeping genes.

The kit may optionally include one or more other reagents required to conduct a biological procedure, such as buffers, salts, enzymes, enzyme co-factors, substrates, detection reagents, washing reagents, and the like. Additional components, such as buffers and solutions for the isolation and/or treatment of a test sample, may also be included in the kit. The kit may additionally include one or more control sequences or samples.

One or more of the components of the kit may optionally be lyophilised and the kit may further comprise reagents suitable for the reconstitution of the lyophilised component(s).

The various components of the kit are provided in suitable containers. In some embodiments, the container may itself be a suitable vessel for carrying out the biological procedure, for example, a microtitre plate. Where appropriate, the kit may also optionally contain reaction vessels, mixing vessels and other components that facilitate the preparation of reagents or a test sample, or the carrying out of the biological procedure. The kit may also include one or more instruments for assisting with obtaining a test sample, such as a syringe, pipette, forceps, or the like.

In some embodiments, reagents comprised by the kit or their containers may be colour-coded to facilitate their use. When reagents are colour-coded, addition of one reagent to another in a particular step may for example result in a change in the colour of the mixture, thus providing an indication that the step was carried out.

The kit can optionally include instructions for use, which may be provided in paper form, in computer-readable form, such as a CD, DVD, USB stick or the like, or in the form of directions or instructions for accessing a website. The kit may also comprise computer readable media comprising software, or directions or instructions for accessing a website that provides software, to assist in the interpretation of results obtained from using the kit.

Certain embodiments of the invention relate to microarrays for detection of a plurality of ETSGs. In one embodiment, the microarrays comprise a plurality of polynucleotide probes attached to a solid support, each of the polynucleotide probes capable of specifically hybridizing to an expression product (or complement thereof) of a respective one of the plurality of ETSGs. The microarray may optionally include one or more control probes, for example, probes capable of detecting the expression of housekeeping genes. In some embodiments, the microarray may further comprise probes for a plurality of Inflammatory Signature genes, for example, selected from those identified in Table 4. For microanalysis, probe sequences are typically between about 15 and about 100 nucleotides in length, for example, between about 15 and about 90 nucleotides in length, between about 15 and about 80 nucleotides in length, between about 15 and about 70 nucleotides in length, between about 15 and about 60 nucleotides in length, or between about 20 and about 60 nucleotides in length. By way of example only and not meant to be limiting, generally probe sequences comprise about 25 nt in Affymetrix arrays, and about 60 nt in Agilent arrays.

In certain embodiments, the microarray comprises a plurality of nucleic acid probes capable of hybridizing to cDNAs that comprise nucleotide sequences complementary to mRNAs encoded by a plurality of ETSGs.

In some embodiments, the microarray consists essentially of nucleic acid probes capable of hybridizing to cDNAs that comprise nucleotide sequences complementary to mRNAs encoded by a plurality of ETSGs. In some embodiments, the microarray consists essentially of (i) nucleic acid probes capable of hybridizing to cDNAs that comprise nucleotide sequences complementary to mRNAs encoded by a plurality of ETSGs, and (ii) nucleic acid probes capable of hybridizing to cDNAs that comprise nucleotide sequences complementary to mRNAs encoded by a partial set of non-ETSGs. In some embodiments, the microarray consists essentially of (i) nucleic acid probes capable of hybridizing to cDNAs that comprise nucleotide sequences complementary to mRNAs encoded by a plurality of ETSGs, and (ii) nucleic acid probes capable of hybridizing to cDNAs that comprise nucleotide sequences complementary to mRNAs encoded by a partial set of housekeeping genes. In some embodiments, the microarray consists essentially of (i) nucleic acid probes capable of hybridizing to cDNAs that comprise nucleotide sequences complementary to mRNAs encoded by a plurality of ETSGs, and (ii) nucleic acid probes capable of hybridizing to cDNAs that comprise nucleotide sequences complementary to mRNAs encoded by a plurality of Inflammatory Signature genes. In some embodiments, the microarray consists essentially of (i) nucleic acid probes capable of hybridizing to cDNAs that comprise nucleotide sequences complementary to mRNAs encoded by a plurality of ETSGs, (ii) nucleic acid probes capable of hybridizing to cDNAs that comprise nucleotide sequences complementary to mRNAs encoded by a plurality of Inflammatory Signature genes, and (iii) nucleic acid probes capable of hybridizing to cDNAs that comprise nucleotide sequences complementary to mRNAs encoded by a partial set of housekeeping genes. In some embodiments, the microarray consists essentially of (i) nucleic acid probes capable of hybridizing to cDNAs that comprise nucleotide sequences complementary to mRNAs encoded by a plurality of ETSGs, (ii) nucleic acid probes capable of hybridizing to cDNAs that comprise nucleotide sequences complementary to mRNAs encoded by a plurality of Inflammatory Signature genes, and (iii) nucleic acid probes capable of hybridizing to cDNAs that comprise nucleotide sequences complementary to mRNAs encoded by a partial set of non-ETSGs.

In some embodiments, the microarray consists of nucleic acid probes capable of hybridizing to cDNAs that comprise nucleotide sequences complementary to mRNAs encoded by a plurality of ETSGs. In some embodiments, the microarray consists of (i) nucleic acid probes capable of hybridizing to cDNAs that comprise nucleotide sequences complementary to mRNAs encoded by a plurality of ETSGs, and (ii) nucleic acid probes capable of hybridizing to cDNAs that comprise nucleotide sequences complementary to mRNAs encoded by a partial set of non-ETSGs. In some embodiments, the microarray consists of (i) nucleic acid probes capable of hybridizing to cDNAs that comprise nucleotide sequences complementary to mRNAs encoded by a plurality of ETSGs, and (ii) nucleic acid probes capable of hybridizing to cDNAs that comprise nucleotide sequences complementary to mRNAs encoded by a partial set of housekeeping genes. In some embodiments, the microarray consists of (i) nucleic acid probes capable of hybridizing to cDNAs that comprise nucleotide sequences complementary to mRNAs encoded by a plurality of ETSGs, and (ii) nucleic acid probes capable of hybridizing to cDNAs that comprise nucleotide sequences complementary to mRNAs encoded by a plurality of Inflammatory Signature genes. In some embodiments, the microarray consists of (i) nucleic acid probes capable of hybridizing to cDNAs that comprise nucleotide sequences complementary to mRNAs encoded by a plurality of ETSGs, (ii) nucleic acid probes capable of hybridizing to cDNAs that comprise nucleotide sequences complementary to mRNAs encoded by a plurality of Inflammatory Signature genes, and (iii) nucleic acid probes capable of hybridizing to cDNAs that comprise nucleotide sequences complementary to mRNAs encoded by a partial set of housekeeping genes. In some embodiments, the microarray consists of (i) nucleic acid probes capable of hybridizing to cDNAs that comprise nucleotide sequences complementary to mRNAs encoded by a plurality of ETSGs, (ii) nucleic acid probes capable of hybridizing to cDNAs that comprise nucleotide sequences complementary to mRNAs encoded by a plurality of Inflammatory Signature genes, and (iii) nucleic acid probes capable of hybridizing to cDNAs that comprise nucleotide sequences complementary to mRNAs encoded by a partial set of non-ETSGs.

In some embodiments, the number of nucleic acid probes capable of hybridizing to cDNAs that comprise nucleotide sequences complementary to mRNAs encoded by a plurality of ETSGs is greater than the number of other nucleic acid probes of the microarray. In some embodiments, the number of nucleic acid probes capable of hybridizing to cDNAs that comprise nucleotide sequences complementary to mRNAs encoded by ETSGs plus the number of nucleic acid probes capable of hybridizing to cDNAs that comprise nucleotide sequences complementary to mRNAs encoded by Inflammatory Signature genes is greater than the number of other nucleic acid probes of the microarray.

In some embodiments, the plurality of ETSGs are selected from the ETSGs listed in Table 1. In some embodiments, the plurality of ETSGs comprise C19orf59, CCL22, CD14, CD300LF, CYP1B1, DHRS9, FCER1G, FPR1, FPR2, GK, HIS 1H2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR. In some embodiments, the plurality of Inflammatory Signature genes are selected from the genes listed in Table 4.

In certain embodiments, a microarray includes probes for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1.

In certain embodiments, the plurality of probes of a microarray that are specific for ETSGs comprise probes for ETSGs selected from Table 1.

In certain embodiments, the plurality of probes of a microarray that are specific for ETSGs consists of probes for ETSGs selected from Table 1.

In certain embodiments, the plurality of probes of a microarray that are specific for ETSGs consists of probes for all the ETSGs in Table 1.

In certain embodiments, the plurality of probes of a microarray that are specific for ETSGs comprises probes for ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of probes of a microarray that are specific for ETSGs consists of probes for ETSGs selected from C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, the plurality of probes of a microarray that are specific for ETSGs consists of probes for each of the following: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In certain embodiments, a microarray includes probes for 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the following ETSGs: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDL1M7, PLAUR, PSTPIP2, RAB13, RETN, RHBDD2, S100A4, S100A9, S100A12, SERPINA1, UPP1, CPVL, CST3, LY86 and PROCR.

Further Aspects and Embodiments

Also disclosed herein are the following further aspects and embodiments of the invention:

In one embodiment, there is provided a method of identifying a patient who has severe sepsis or is at high risk of developing severe sepsis comprising obtaining a biological sample from the individual and determining the level of expression of at least two or more genes from the endotoxin tolerance signature whereby the risk of sepsis, severe sepsis or organ failure is indicated by the altered expression of endotoxin tolerance signature genes relative to the expression of the same genes in non-sepsis individuals.

In one aspect, the invention provides a method of identifying a patient who has severe sepsis or is at high risk of developing severe sepsis, comprising obtaining a biological sample from the patient and determining the level of expression of at least two, or at least three, or at least four, or at least five, or at least six, or at least seven, or at least eight, or at least nine, or at least ten, or at least eleven, or at least twelve, or at least thirteen, or at least fourteen, or at least fifteen different Endotoxin Tolerance Signature Genes (ETSGs) in the biological sample, whereby the presence or high risk of severe sepsis is indicated by the level of expression of the ETSGs. In one embodiment the level of expression of more than 15 different ETGSs is determined. In one embodiment the level of expression of more than 20 different ETGSs is determined. In one embodiment the level of expression of more than 25 different ETGSs is determined. In one embodiment the level of expression of more than 30 different ETGSs is determined. In one embodiment the level of expression of about 31 different ETGSs is determined.

In one embodiment, at least two, or at least three, or at least four, or at least five, or at least six, or at least seven, or at least eight, or at least nine, or at least ten, or at least eleven, or at least twelve, or at least thirteen, or at least fourteen, or at least fifteen, or up to 31 of the ETSGs are selected from the group consisting of RNASE1, ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1, and VCAN.

In certain embodiments, the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1 is determined.

In certain embodiments, the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the following ETSGs is determined: C19orf39, CCL22, CD14, CD300LF, CYP1B1, DHRS9, FCER1G, FPR1, FPR2, GK, HISTH2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In one embodiment, the method further comprises determining the level of expression of the same ETSGs in a control sample from an individual who does not have sepsis. Where the expression levels of the ETSGs from the patient sample and the control sample are different, the patient is identified as having severe sepsis or being at high risk for severe sepsis.

In one embodiment, the patient has not yet been definitively diagnosed as having severe sepsis. In another embodiment, the patient has already been diagnosed with severe sepsis.

In one embodiment, the biological sample is selected from a group consisting of blood, tissue, amniotic fluid, saliva, urine, amniotic fluid, bronchoalveolar lavage fluid, and skin cells.

In one embodiment, the identification of a patient with severe sepsis is used to guide optimal therapy for the patient.

In one embodiment, the level of ETSG expression is determined by assessing the RNA or cDNA level in the biological sample. In one embodiment, the level of ETSG expression is determined using one or more methods selected from the polymerase chain reaction (PCR), reverse transcriptase-(RT) PCR, Q-beta replicase amplification, ligase chain reaction, nucleic acid sequence amplification, signal amplification (Ampliprobe), light cycling and other variations of PCR or non-PCR based amplification methods, differential display, Northern analysis, hybridization, microarrays, DNA sequencing, RNA-Seq, nucleic acid sequencing, MassArray analysis, and MALDI-TOF mass spectrometry.

In one aspect, the invention provides a method of identifying an individual who is at risk of organ failure, comprising obtaining a biological sample from the individual and determining the level of expression of at least two, or at least three, or at least four, or at least five, or at least six, or at least seven, or at least eight, or at least nine, or at least ten, or at least eleven, or at least twelve, or at least thirteen, or at least fourteen, or at least fifteen different ETSGs in the biological sample whereby the risk of organ failure is indicated by the level of expression of the ETSGs. In one embodiment the level of expression of more than 15 different ETGSs is determined. In one embodiment the level of expression of more than 20 different ETGSs is determined. In one embodiment the level of expression of more than 25 different ETGSs is determined. In one embodiment the level of expression of more than 30 different ETGSs is determined. In one embodiment the level of expression of about 31 different ETGSs is determined.

In one embodiment, the method further comprises determining the level of expression of the same ETSGs in a control sample from an individual who docs not have sepsis. Where the expression levels of the ETSGs from the patient sample and the control sample are different, the patient is identified as having a risk of organ failure.

In one embodiment, at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 of the ETSGs are selected from the group consisting of RNASE1, ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1, and VCAN.

In certain embodiments, the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1 is determined.

In certain embodiments, the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the following ETSGs is determined: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDL1M7, PLAUR, PSTPIP2, RAB13, RETN, RHBDD2, S100A4, S100A9, S100A12, SERPINA1, UPP1, CPVL, CST3, LY86 and PROCR.

In one aspect, the invention provides a method for treating severe sepsis, comprising identifying a patient who has severe sepsis or is at high risk of developing severe sepsis and treating said patient with at least one potent antibiotic that is indicated for the treatment of severe sepsis. In one embodiment, patient identification comprises obtaining a biological sample from the patient and determining the level of expression of at least two, or at least three, or at least four, or at least five, or at least six, or at least seven, or at least eight, or at least nine, or at least ten, or at least eleven, or at least twelve, or at least thirteen, or at least fourteen, or at least fifteen different ETSGs in the biological sample, whereby the presence or high risk of severe sepsis is indicated by the level of expression of said at least two ETSGs. In one embodiment the level of expression of more than 15 different ETGSs is determined. In one embodiment the level of expression of more than 20 different ETGSs is determined. In one embodiment the level of expression of more than 25 different ETGSs is determined. In one embodiment the level of expression of more than 30 different ETGSs is determined. In one embodiment the level of expression of about 31 different ETGSs is determined.

In one embodiment, at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 of the ETSGs are selected from the group consisting of RNASE1, ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1, and VCAN.

In certain embodiments, the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the ETSGs in Table 1 is determined.

In certain embodiments, the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 of the following ETSGs is determined: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In one embodiment, the method further comprises determining the level of expression of the same ETSGs in a control sample from an individual who does not have sepsis. Where the expression levels of the ETSGs from the patient sample and the control sample are different, the patient is identified as having severe sepsis and a therapeutically effective dose of at least one potent antibiotic that is indicated for the treatment of severe sepsis is administered to the patient.

In one aspect, the invention provides a test kit for the identification of severe sepsis, comprising at least two, or at least three, or at least four, or at least five, or at least six, or at least seven, or at least eight, or at least nine, or at least ten, or at least eleven, or at least twelve, or at least thirteen, or at least fourteen, or at least fifteen different nucleic acids, each of which comprises a nucleotide sequence that corresponds to or is complementary to the nucleotide sequence of a different ETSG. In one embodiment the kit comprises more than 15 different nucleic acids. In one embodiment the kit comprises more than 20 different nucleic acids. In one embodiment the kit comprises more than 25 different nucleic acids. In one embodiment the kit comprises more than 30 different nucleic acids. In one embodiment the kit comprises about 31 different nucleic acids.

In one embodiment, the kit comprises at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different nucleic acids, each of which comprises a nucleotide sequence that corresponds to or is complementary to the nucleotide sequence of a different ETSG, wherein the ETSGs are selected from the group consisting of RNASE1, ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, REIN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1, and VCAN.

In certain embodiments, the kit comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 different nucleic acids, each of which comprises a nucleotide sequence that corresponds to or is complementary to the nucleotide sequence of a different ETSG in Table 1.

In certain embodiments, the kit comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 different nucleic acids, each of which comprises a nucleotide sequence that corresponds to or is complementary to the nucleotide sequence of one of the following ETSGs: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In one aspect, the invention provides a test kit for identifying an individual who is at high risk of developing severe sepsis, comprising at least two, or at least three, or at least four, or at least five, or at least six, or at least seven, or at least eight, or at least nine, or at least ten, or at least eleven, or at least twelve, or at least thirteen, or at least fourteen, or at least fifteen different nucleic acids, each of which comprises a nucleotide sequence that corresponds to or is complementary to the nucleotide sequence of a different ETSG. In one embodiment the kit comprises more than 15 different nucleic acids. In one embodiment the kit comprises more than 20 different nucleic acids. In one embodiment the kit comprises more than 25 different nucleic acids. In one embodiment the kit comprises more than 30 different nucleic acids. In one embodiment the kit comprises about 31 different nucleic acids.

In one embodiment, the kit comprises at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different nucleic acids, each of which comprises a nucleotide sequence that corresponds to or is complementary to the nucleotide sequence of a different ETSG, wherein the ETSGs are selected from the group consisting of RNASE1, ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDL1M7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1, and VCAN.

In certain embodiments, the kit comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 different nucleic acids, each of which comprises a nucleotide sequence that corresponds to or is complementary to the nucleotide sequence of a different ETSG in Table 1.

In certain embodiments, the kit comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 different nucleic acids, each of which comprises a nucleotide sequence that corresponds to or is complementary to the nucleotide sequence of one of the following ETSGs: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In one aspect, the invention provides a test kit for identifying an individual who is at risk of organ failure, comprising at least two, or at least three, or at least four, or at least five, or at least six, or at least seven, or at least eight, or at least nine, or at least ten, or at least eleven, or at least twelve, or at least thirteen, or at least fourteen, or at least fifteen different nucleic acids, each of which comprises a nucleotide sequence that corresponds to or is complementary to the nucleotide sequence of a different ETSG. In one embodiment the kit comprises more than 15 different nucleic acids. In one embodiment the kit comprises more than 20 different nucleic acids. In one embodiment the kit comprises more than 25 different nucleic acids. In one embodiment the kit comprises more than 30 different nucleic acids. In one embodiment the kit comprises about 31 different nucleic acids.

In one embodiment, the kit comprises at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different nucleic acids, each of which comprises a nucleotide sequence that corresponds to or is complementary to the nucleotide sequence of a different ETSG, wherein the ETSGs are selected from the group consisting of RNASE1, ADAM15, ADAMDEC1, ALCAM, ALDH1A1, ANKRD1, C19orf59, CA12, CAMP, CCL1, CCL19, CCL22, CCL24, CCL7, CD14, CD300LF, CD93, CDK5RAP2, CPVL, CST3, CST6, CTSK, CXCL10, CYP1B1, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3, HPSE, HSD11B1, HTRA1, IL18BP, IL3RA, ITGB8, KIAA1199, LILRA3, LILRA5, LIPA, LY86, MARCO, MGST1, MMP7, MT1F, MT1G, MT1H, MT1M, MT1X, MXD1, MYADM, NEFH, NQO1, NRIP3, OLIG2, PANX2, PAPLN, PDL1M7, PLAUR, PLD3, PPBP, PROCR, PSTPIP2, PTGES, PTGR1, RAB13, RARRES1, RETN, RHBDD2, RNASE1, S100A12, S100A4, S100A8, S100A9, SERPINA1, SERPINB7, SLC16A10, SLC7A11, TGM2, TLR7, TMEM158, TREM1, TSPAN4, UPP1, and VCAN.23.

In certain embodiments, the kit comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 different nucleic acids, each of which comprises a nucleotide sequence that corresponds to or is complementary to the nucleotide sequence of a different ETSG in Table 1.

In certain embodiments, the kit comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 different nucleic acids, each of which comprises a nucleotide sequence that corresponds to or is complementary to the nucleotide sequence of one of the following ETSGs: C19orf59, CCL22, CD14, CD300LF, CYP1B1, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86 and PROCR.

In one embodiment, the test kits of the invention further comprise instructions for use, a sample collection device, one or more reagents for sample preparation, and a positive control sample.

In one embodiment, the test kits of the invention further comprise instructions for use, a sample collection device, one or more reagents for sample preparation, and a negative control sample.

In one embodiment, the test kits of the invention further comprise instructions for use, a sample collection device, one or more reagents for sample preparation, and a negative control sample and a positive control sample.

In one aspect, the invention provides a method of treating a patient with severe sepsis, comprising administering to the patient a therapeutically effective amount of an agent that counteracts endotoxin tolerance by changing the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in a cell from the individual.

In one embodiment, the agent is selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the agent is an immune cell.

In one aspect, the invention provides a method of preventing or delaying severe sepsis in a patient, comprising administering to the patient an effective amount of an agent that counteracts endotoxin tolerance by changing the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or up to 99 different ETSGs in a cell from the patient.

In one embodiment, the agent is selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the agent is an immune cell.

In one aspect, the invention provides a method of treating severe sepsis in a patient, comprising administering to the patient a therapeutically effective amount of an agent that counteracts endotoxin tolerance by changing the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in a cell from the patient, and further comprises monitoring the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in samples taken from the patient during therapy.

In one embodiment, the agent is selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the agent is an immune cell.

In one aspect, the invention provides a method of preventing or delaying severe sepsis in a patient, comprising administering to the patient an effective amount of an agent that counteracts endotoxin tolerance by changing the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in a cell from the patient, and further comprises monitoring the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in samples taken from the patient during preventative treatment.

In one embodiment, the agent is selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the agent is an immune cell.

In one aspect, the invention provides a method of preventing or delaying organ failure in a patient, comprising administering to the patient an effective amount of an agent that counteracts endotoxin tolerance by changing the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in a cell from the patient, and further comprises monitoring the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in samples taken from the patient during preventative treatment.

In one embodiment, the agent is selected from the group consisting of Interferon gamma; CpG-ODN with or without IL-10; anti-CD40; inhibitors of STATS, STATE, p50 NFκB, and IKK3; imidazoquinolines; and zoledronic acid. In one embodiment, the agent is an immune cell.

In one aspect, the invention provides a method of treating severe sepsis, comprising administering to a patient a therapeutically effective amount of an agent selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the method further comprises monitoring the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in samples taken from the patient during therapy.

In one aspect, the invention provides a method of preventing or delaying severe sepsis, comprising administering to a patient an effective amount of an agent selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the method further comprises monitoring the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in samples taken from the patient during preventative treatment.

In one aspect, the invention provides a method of preventing or delaying organ failure, comprising administering to a patient an effective amount of an agent selected from the group consisting of Interferon gamma; CpG-ODN with or without IL-10; anti-CD40; inhibitors of STAT3, STATE, p50 NFκB, and IKKβ; imidazoquinolines; and zoledronic acid. In one embodiment, the method further comprises monitoring the expression of at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in samples taken from the patient during preventative treatment.

In one aspect, the invention provides a method of identifying an agent that is capable of treating sepsis, comprising contacting a cell with the agent and determining the expression of at least two, or at least three, or at least four, or at least five, or at least six, or at least seven, or at least eight or at least nine, or at least ten, or at least eleven, or at least twelve, or at least thirteen, or at least fourteen, or at least fifteen different ETSGs in the cell.

In one embodiment, the cell is an endotoxin tolerant cell. In one embodiment, the method further comprises contacting the cell with an endotoxin following contact of the cell with agent. In one embodiment, the endotoxin is bacterial lipopolysaccharide or lipoteichoic acid. In one embodiment, the bacterial lipopolysaccharide or lipoteichoic acid is present in a bacterium.

In one embodiment agents of the invention are obtained by contacting a cell with a suitable dose of endotoxin, waiting 18 hours and then contacting the cell again with a similar dose of the same or another endotoxin to create an endotoxin tolerant cell, then incubating the endotoxin tolerant cell with an agent of the invention and examining the restoration of cellular ability to interact with a third dose of endotoxin (breaking tolerance).

In one embodiment, the method further comprises contacting a second cell with Interferon gamma; CpG-ODN with or without IL-10; anti-CD40; an inhibitor of STAT3, STATE, p50 NFκB, or IKKβ; an imidazoquinoline; or zoledronic acid, and determining the expression of the same ETSGs in the second cell.

In one embodiment, the method further comprises assaying the agent for the ability to alter macrophage phenotype from M2 to M1.

Agents of the invention may be obtained by contacting a cell with a suitable dose of endotoxin, waiting 18 hours and then contacting the cell again with a similar dose of the same or another endotoxin to create an endotoxin tolerant cell, then incubating the endotoxin tolerant cell with an agent of the invention and examining the restoration of cellular ability to interact with a third dose of endotoxin (breaking tolerance). In one embodiment, the endotoxin is bacterial lipopolysaccharide or lipoteichoic acid.

In one aspect, the invention provides an agent capable of treating sepsis, which agent is identified by a method of the invention. In one embodiment, the agent is capable of altering macrophage phenotypes from M2 to M1.

In one aspect, the invention provides a method for treating sepsis by suppressing endotoxin tolerance. In one embodiment, an agent that is capable of changing the expression of at least one, or at least two, or at least three, or at least four, or at least five, or at least six, or at least seven, or at least eight, or at least nine, or at least ten, or at least eleven, or at least twelve, or at least thirteen, or at least fourteen, or at least fifteen, or at least 31 different ETSGs in a cell from a patient is used.

To gain a better understanding of the invention described herein, the following examples are set forth. It will be understood that these examples are intended to describe illustrative embodiments of the invention and are not intended to limit the scope of the invention in any way.

EXAMPLES

Methods

Overview:

Endotoxin Tolerance and Inflammatory LPS gene signatures were derived from published [Pena O M, et al. Journal of Immunology 2011; 186:7243-54] microarray analyses of human PBMC identifying differentially expressed genes compared to control PBMCs. To enable more direct comparisons between signatures, differentially expressed inflammatory genes were further reduced from 178 to 93 genes by overlap with an experimental endotoxaemia microarray dataset (GSE3284) [Calvano et al., Nature, 2005, 437:1032-1037] from the PBMC of healthy individuals stimulated with low-dose LPS in vivo at 2 and 6 hours. Analysis of the 'Endotoxin Tolerance' and 'Inflammatory' signatures in patients and controls was performed using the statistically rigorous gene set test ROAST [Wu D, et al. Bioinformatics 2010; 26:2176-82]. The selection of datasets was based on the following inclusion criteria: 1) Cross-sectional or longitudinal cohort studies. 2) Whole blood or purified leukocyte populations. 3) Pediatric or adult patients. 4) Healthy subjects used as controls. 5) Only datasets published in a scientific journal. Normalized datasets were downloaded from NCBI GEO using the Bioconductor package GEOquery [Davis S, Meltzer P S. Bioinformatics 2007; 23:1846-7], All data processing was performed in R using Bioconductor [Gentleman R C, et al. Genome Biology 2004; 5:R80]. For the RNA Seq study reported here, 73 patients (age 60±17; 46 males, 27 females) were recruited with deferred consent according to UBC human ethics approval at the time of first examination in an emergency ward based on the opinion of physicians that there was a potential for the patient's condition to develop into sepsis. After the first blood draw, total RNA was prepared from whole blood, converted to cDNA, sequenced on an Illumina Genome Analyzer IIx, mapped to the human genome and converted into expression Tables by standard methods. Normalization used the Limma package function voom. All other clinical parameters based on routine tests were obtained by examination of patient's charts.

Meta-Analysis Datasets.

Searches for sepsis datasets were performed in the public repositories NCBI GEO and EBI Array Express. The selection of datasets (Table 2) was based on the following inclusion criteria: 1) Cross-sectional or longitudinal cohort studies. 2) Whole blood or purified leukocyte populations. 3) Pediatric or adult patients. 4) Healthy subjects used as controls. 5) Only datasets published as part of a study in a scientific journal. A list of the datasets accessed is given in Table 2.

TABLE 2

Description of re-analyzed public sepsis datasets*

| N* | GEO ID (GSE #) | Samples selected | Samples (Sepsis/Controls) | Location; Cell Type; Time of sample collection | Pubmed #; Year | Array Platform |
|---|---|---|---|---|---|---|
| 1 | 28750 | Used only samples from sepsis subjects and healthy controls. Post-surgery subject group were excluded from the analysis. | 10/20 | Australia; Leukocytes; ICU <24 H> | 21682927; 2011 | A |
| 2 | 13015 | Used only samples with sepsis due to organisms other than *B. pseudomallei*, Controls were healthy without comorbidities. | 24/3 | Thailand; Whole blood; Within 24 h of sepsis diagnosis | 19903332; 2009 | B |
| 3 | 9692 | Used all samples provided by the study. | 30/15 | USA; Leukocytes; ICU <24 H> | 18460642; 2007 | A |
| 4 | 26378 | Used all samples provided by the study. | 82/21 | USA; Leukocytes; ICU <24 H> | 21738952; 2011 | A |
| 5 | 26440 | Used all samples provided by the study. | 98/32 | USA; Leukocytes; ICU <24 H> | 21738952; 2011 | A |
| 6 | 4607 | Used only samples from subjects undergoing septic shock collected at day 1 and day 3 post-ICU admission. SIRS & SIRS-resolved subject samples were excluded. | 69/15 | USA; Leukocytes; ICU <24 H> | 17374846; 2006 | A |
| 7 | 8121 | Used all samples provided by the study. | 60/15 | USA; Leukocytes; ICU <24 H> | 17932561; 2007 | A |
| 8 | 11755 | Used only samples from septic subjects after 24 hours (day 1) and 72 hours (day 3) of ICU admission. Samples taken at 8 hours post-admission were excluded from the analysis. | 5/3 | Netherlands; Leukocytes; ICU <24 H> | 23842590; 2008 | A |
| 9 | 13904 | Used only Samples from sepsis and septic shock subjects. SIRS subjects were excluded from analysis. | 158/18 | USA Leukocytes; ICU <24 H> | 19325468; 2008 | A |

Table 2 footnotes:
*Microarray data were downloaded from the repository Gene Expression Omnibus (GEO). The associated papers (given by Pubmed number), numbers of patients analyzed and details of the specific studies are presented. The Study description is included as a footnote. Array Platform was A, GPL570 [HG-U133_Plus_2] Affymetrix Human Genome U133 Plus 2.0 Array; B. GPL6947 Illumina HumanHT-12 V3.0 expression beadchip.
STUDY DESIGN by study in column 1 of Table 2:
1. GSE 28750. Cross-sectional. Multi-centre, prospective clinical trial conducted across 4 tertiary critical care settings in Australia. Sepsis patients were recruited if they met the 1992 Consensus Statement criteria and had clinical evidence of systemic infection based on microbiology diagnoses. Healthy subjects were used as normal controls in the study.
2. GSE 13015. Cross-sectional. Study of patients with sepsis with a positive blood culture due to *Burkoldheria pseudomallei*, and sepsis due to other organisms cf. non-infected controls
3. GSE 9692. Cross-sectional. Children <10 yr of age admitted to the pediatric intensive care unit (PICU), with pediatric-specific criteria for septic shock. Normal control patients were recruited from the participating institutions using the following exclusion criteria: a recent febrile illness (within 2 wk), recent use of anti-inflammatory medications (within 2 wks), or any history of chronic or acute disease associated with inflammation.
4. GSE 26378. Cross-sectional. Expression data from children with septic shock was generated using whole blood-derived RNA samples representing the first 24 hours of admission to the PICU. Healthy subjects (children) were used as normal controls in the study.
5. GSE 26440. Cross-sectional. Expression data from children with septic shock were generated using whole blood-derived RNA samples representing the first 24 hours of admission to the PICU. Healthy subjects (children) were used as normal controls in the study.
6. GSE 4607. Longitudinal. Children <10 years of age admitted to the pediatric intensive care unit and meeting the criteria for either SIRS or septic shock were eligible for the study. Control patients were recruited from the outpatient or inpatient departments of the participating institutions using the following exclusion criteria: a recent febrile illness (within 2 weeks), recent use of anti-inflammatory medications (within 2 weeks), or any history of chronic or acute disease associated with inflammation.
7. GSE 8121. Longitudinal. Genome-level expression profiles were generated from whole blood-derived RNA of children with septic shock corresponding to day 1 and day 3 of septic shock, respectively. Control patients were recruited from the participating institutions using the following exclusion criteria: a recent febrile illness (within two weeks), recent use of anti-inflammatory medications (within two weeks), or any history of chronic or acute disease associated with inflammation.
8. GSE 11755. Longitudinal. Prospective case-control study, six children with meningococcal sepsis were included. Blood was drawn at four time points (t = 0, t = 8, t = 24 and t = 72 h after admission to the pediatric intensive care unit. Healthy subjects (children) were used as normal controls in the study.
9. GSE 13904. Longitudinal. Genome-level expression profiles of critically ill children representing the systemic inflammatory response syndrome (SIRS), sepsis, and septic shock spectrum at day 1 and day 3 post-admission. Healthy subjects (children) were used as normal controls in the study.

Patient Selection and Study Design.

In the blinded, observational, controlled cohort study, patients with suspected sepsis, based on the opinion of the attending physician, were enrolled from St. Paul's Hospital, Vancouver Canada, at the first clinical suspicion of sepsis. To determine the appropriate sample size for this study a standard power calculation was used for adequate sensitivity [Jones S R, S Carley, and M Harrison. Emergency medicine Journal 2003; 20, 453-458, 2003]. To achieve a sensitivity of at least 0.9 at a 95% confidence level, a required sample size of 35 sepsis patients and 70 patients total (assuming 50% of patient with a suspicion of sepsis actually have sepsis) was estimated. 72 total patients were recruited, which were proved subsequently to include 37 sepsis patients. The sole inclusion criterion for this study was the suspicion of sepsis upon observation of the attending physician. The majority of patients (83%) were enrolled from the emergency room. As shown in Table 3, these individuals were heterogeneous. UBC ethical approval protocol enabled deferred consent allowing early patient recruitment in cohorts that spanned from non-infected to septic shock. As controls, consenting healthy individuals, with no evidence of infection, who were scheduled for non-urgent surgery were recruited. Blood was collected in EDTA tubes at the time of initial blood culture, and immediately placed on ice. Plasma and buffy coat were separated and two 1-ml aliquots transferred into bar-coded cryovials at −20° C. until they were transferred to a secure, alarmed −80° C. freezer. Study identification numbers were assigned on these secured enrolment forms and used during all subsequent analyses; thus researchers analyzing gene expression in these patients were blinded as to patient identity or clinical course, which was only revealed during final data analysis. Clinical data was stored in an ORACLE-based database on a firewalled, RSS encrypted server at St Paul's Hospital.

Clinical data was collected retrospectively by physician researchers blinded to the RNA-Seq data. New organ dysfunction was defined based on laboratory values collected in the electronic medical record system. Acute organ failures assessed were the presence of shock (treatment with a vasopressor), acute respiratory distress syndrome (need for mechanical ventilation), coagulopathy (platelet count <80/µL), hepatic failure (total bilirubin>34 µmol/L) and acute kidney injury (a serum creatinine rise ≥26.5 µmol/L or ≥1.5 fold from baseline. Initial vital signs were retrospectively extracted from the paper records.

TABLE 3

Details of individual patients recruited for controlled cohort study

| | | | | Diagnostic Criteria[2] | | | | | |
|---|---|---|---|---|---|---|---|---|---|
| Lab ID | ICU or non-ICU[1] | No. of organ failures* | Micro-biology[§] | Triage blood pressure systolic/ diastolic | Initial WBC | Triage Temp/° C. | Triage Heart Rate | Triage Respiratory Rate | First Partial $CO_2$ |
| SEPSIS GROUP | | | | | | | | | |
| 612920 | ICU | 4 | Positive | 94/62 | 17 | 37.8 | 170 | 40 | NA[3] |
| 154114 | ICU | 3 | Positive | 73/45 | 22.4 | 36.7 | 73 | 32 | 38 |
| 297580 | ICU | 4 | Positive | 86/40 | 10.4 | 35.3 | 56 | 16 | 30 |
| 212463 | ICU | 3 | Positive | 165/101 | 19.1 | 37.5 | 98 | 34 | 71 |
| 708631 | ICU | 2 | Positive | 100/61 | 8 | 38.2 | 96 | 10 | 42 |
| 799587 | ICU | 5 | Positive | 84/45 | 7.2 | 37 | 127 | 22 | 25 |
| 795380 | ICU | 3 | Positive | 139/90 | 4.2 | 30.4 | 53 | 22 | 61 |
| 913994 | ICU | 4 | Positive | 81/62 | 10.4 | 39.3 | 139 | 40 | 26 |
| 889485 | ICU | 4 | Positive | 67/53 | 16.3 | 36.1 | 142 | 26 | 30 |
| 137731 | ICU | 3 | Positive | 130/78 | 19.8 | 36.4 | 100 | 16 | 52 |
| 862476 | ICU | 4 | Positive | 136/80 | 25.8 | 39.2 | 110 | 30 | 49 |
| 864637 | ICU | 4 | Positive | 83/54 | 11.3 | 37.2 | 126 | 26 | 51 |
| 980414 | ICU | 3 | Positive | 112/62 | 26.3 | 37.9 | 126 | 44 | 35 |
| 375523 | ICU | 4 | Positive | 134/58 | 37.7 | 38.5 | 133 | 34 | NA |
| 364132 | Non-ICU | 0 | Positive | 98/68 | 9.4 | 38.3 | 119 | 22 | NA |
| 450578 | Non-ICU | 0 | Positive | 86/44 | 18.4 | 37.7 | 86 | 18 | NA |
| 694402 | Non-ICU | 1 | Positive | 175/81 | 2.2 | 37.4 | 118 | 22 | NA |
| 732740 | Non-ICU | 2 | Positive | 155/83 | 3.2 | 37.1 | 107 | 22 | NA |
| 826967 | Non-ICU | 1 | Positive | 129/66 | 23.8 | 37.2 | 109 | 20 | NA |
| 300271 | ICU | 3 | Negative | 103/57 | 15.3 | 36.7 | 102 | 22 | 42 |
| 679797 | ICU | 3 | Negative | 96/57 | 40 | 36.9 | 127 | 24 | NA |
| 266144 | ICU | 4 | Negative | 217/121 | 2.1 | 36.5 | 135 | 20 | 28 |
| 602395 | ICU | 3 | Negative | 105/95 | 12.9 | 37.5 | 92 | NA | 37 |
| 476146 | ICU | 3 | Negative | 106 | 15.2 | 36.2 | 105 | —[4] | 44 |
| 853176 | Non ICU | 0 | Negative | 139/69 | 14.4 | 37.1 | 105 | 23 | NA |
| 220171 | Non ICU | 2 | Negative | 76/51 | 3.3 | 39 | 109 | 18 | NA |
| 581691 | Non ICU | 1 | Negative | 102/57 | 19.5 | 36.7 | 105 | 24 | NA |
| 823914 | Non ICU | 0 | Negative | 90/52 | 12.3 | 37.2 | 138 | 28 | NA |
| 155286 | Non ICU | 0 | Negative | 141/79 | 14.8 | 36.4 | 114 | 20 | NA |
| 658301 | Non ICU | 1 | Negative | 114/76 | 16.6 | 36.7 | 119 | 16 | NA |
| 800267 | Non ICU | 1 | Negative | 143/97 | 6.3 | 36.5 | 130 | 24 | NA |
| 235545 | Non ICU | 0 | Negative | 103/78 | 21.8 | 36.4 | 105 | 18 | NA |
| 342306 | Non ICU | 1 | Negative | 120/73 | 12.1 | 36.7 | 136 | 16 | NA |
| 468026 | Non ICU | 0 | Negative | 171/110 | 6.4 | 37.3 | 101 | 22 | NA |
| 522087 | Non ICU | 0 | Negative | 124/62 | 7 | 36.7 | 120 | 38 | NA |
| 716574 | Non ICU | 1 | Negative | 117/89 | 5.8 | 36.4 | 106 | 40 | NA |
| 746024 | Non ICU | 1 | Negative | 91/55 | 19.1 | 37.4 | 90 | 28 | NA |
| NO SEPSIS GROUP | | | | | | | | | |
| 402569 | ICU | 3 | Positive | 123/74 | 10.4 | 37.1 | 74 | 16 | 31 |
| 941715 | Non ICU | 0 | Positive | 119/65 | 5.1 | 36.8 | 82 | 16 | NA |
| 583654 | Non ICU | 0 | Positive | 180/96 | 7.6 | 36.4 | 64 | 20 | NA |
| 237093 | Non ICU | 0 | Positive | 102/58 | 10.3 | 36.6 | 82 | 16 | NA |
| 355472 | Non ICU | 1 | Positive | 147/70 | 13.4 | 38 | 66 | 20 | NA |
| 416442 | Non ICU | 2 | Positive | 133/62 | 7 | 39.5 | 89 | 20 | NA |
| 439362 | Non ICU | 1 | Positive | 146/84 | 5.6 | 36.8 | 89 | 16 | NA |

TABLE 3-continued

Details of individual patients recruited for controlled cohort study

| | | | Diagnostic Criteria[2] | | | | | |
|---|---|---|---|---|---|---|---|---|
| Lab ID | ICU or non-ICU[1] | No. of organ failures* | Micro- biology[§] | Triage blood pressure systolic/ diastolic | Initial WBC | Triage Temp/° C. | Triage Heart Rate | Triage Respiratory Rate | First Partial $CO_2$ |
| 701198 | Non ICU | 1 | Positive | 147/68 | 5.6 | 36.4 | 107 | 18 | NA |
| 583577 | ICU | 2 | Negative | 203/111 | 11.2 | 36 | 85 | 32 | 73 |
| 749752 | ICU | 3 | Negative | 85/50 | 12.3 | 36.6 | 60 | 18 | NA |
| 673143 | ICU | 4 | Negative | 162/87 | 9.1 | 36.8 | 90 | 20 | 40 |
| 362763 | ICU | 3 | Negative | 126/60 | 7.3 | 37 | 90 | —[3] | 39 |
| 377121 | ICU | 1 | Negative | 128/88 | 4.8 | 37.2 | 115 | 20 | 36 |
| 288187 | Non-ICU | 0 | Negative | 95/57 | 9.7 | 36.9 | 98 | 20 | NA |
| 993234 | Non-ICU | 0 | Negative | 152/57 | 6.8 | 36.6 | 88 | 24 | NA |
| 890426 | Non-ICU | 1 | Negative | 135/75 | 8.1 | 37.6 | 105 | 16 | NA |
| 290697 | Non-ICU | 0 | Negative | 100/61 | 8.4 | 36.7 | 91 | 20 | NA |
| 104582 | Non-ICU | 0 | Negative | 140/88 | 17.1 | 36.6 | 74 | 20 | NA |
| 245286 | Non-ICU | 0 | Negative | 136/75 | 5.7 | 36.8 | 105 | 20 | NA |
| 417642 | Non-ICU | 0 | Negative | 120/60 | 6.9 | 36.7 | 77 | 24 | NA |
| 911536 | Non-ICU | 0 | Negative | 123/80 | 4.3 | 39.4 | 90 | 18 | NA |
| 346081 | Non-ICU | 0 | Negative | 167/70 | 2.1 | 36.9 | 72 | 20 | NA |
| 449469 | Non-ICU | 0 | Negative | 127/78 | 5.9 | 37.3 | 104 | 16 | NA |
| 568243 | Non-ICU | 1 | Negative | 159/98 | 6.7 | 36.9 | 93 | 18 | NA |
| 695232 | Non-ICU | 1 | Negative | 142/84 | 19.1 | 37.8 | 90 | 16 | NA |
| 770905 | Non-ICU | 0 | Negative | 123/60 | 13.2 | 35.4 | 73 | 16 | NA |
| 929438 | Non-ICU | 1 | Negative | 170/102 | 12.8 | 37.4 | 83 | 16 | NA |
| 602005 | Non-ICU | 0 | None[5] | 130/66 | 1.8 | 36.6 | 64 | 14 | NA |
| 145305 | Non-ICU | 0 | Negative | 142/75 | 8.4 | 36.8 | 67 | 18 | NA |
| 366713 | Non-ICU | 0 | Negative | 91/58 | 10.8 | 36.6 | 71 | 16 | NA |
| 332278 | Non-ICU | 1 | Negative | 99/59 | 8.5 | 36.6 | 86 | 16 | NA |
| 379752 | Non-ICU | 0 | Negative | 130/69 | 10.6 | 36.9 | 65 | 16 | NA |
| 669339 | Non-ICU | 0 | Negative | 123/80 | 5.9 | 37 | 77 | 16 | NA |
| 310017 | Non-ICU | 0 | Negative | 141/96 | 11.4 | 36.9 | 88 | 20 | NA |
| 504886 | Non-ICU | 0 | Negative | 99/55 | NA | 36.4 | 66 | 16 | NA |

Table 3 Footnotes:
*within 48 hr of suspected sepsis.
[§]most within 48 hr of suspected sepsis.
[1]Indicates whether the patient was transferred to the ICU after first clinical examination.
[2]Diagnostic Criteria for Sepsis as per [Bone R C, R A Balk, F B Cerra, R P Dellinger, A M Fein, W A Knaus, R M Schein, W J Sibbald, ASCC Committee. Definitions for sepsis and organ failure and guidelines for the use of innovative therapies in sepsis. The ACCP/SCCM Consensus Conference Committee. American College of Chest Physicians/Soc Critical Care Medicine. 1992. Chest 2009; 136: e28; Hotchkiss, R S, I E Karl, The pathophysiology and treatment of sepsis. N Engl J Med 2003; 348, 138-150]. Respiratory Rate and Partial $CO_2$ are no longer criteria but were added as additional information.
[3]NA: indicates not available.
[4]Patient was ventilated.
[5]None means no culture was requested.

RNA-Seq.

cDNA libraries were prepared from total RNA according to the TruSeq Stranded Total RNA Sample Prep Kit with Ribo-Zero sample preparation guide (Illumina). Unique adapter indexes (Illumina) were attached during sample prep and samples were run pooled and loaded into a single flow cell lane to reduce technical variability. RNA-Seq was performed on a GAIIx instrument (Illumina), using a single read run with 63 bp long sequence reads (+adapter/index sequences). Raw basecall data was converted to FASTQ sequence files using Off-Line Basecaller 1.9.4 (Ilumina) and a custom Perl script. Reads were aligned to the hg19 human genome with TopHat version 2.06 and Bowtie2 2.0.0-beta6. Reads were initially mapped to Ensembl transcripts with the search for novel junctions disabled. Genomic coordinates were then transformed into counts of protein-coding Ensembl genes. To do this, a chimeric gene-model was first defined by merging all protein-coding transcripts for a given gene. Transcripts that had reads in less than 50% of their exons in all samples were defined as not expressed and were excluded from the chimeric transcriptome. Reads that over-lapped the chimeric genes were counted using the htseq-count script in the intersection-nonempty mode (see EMBL website). The script discards multi-mapped reads as well as reads that overlap multiple distinct genes, to generate a file of uniquely mapped gene counts.

Data Analysis.

All data processing was performed in R using Bioconductor. For the meta-analysis, normalized datasets were downloaded from NCBI GEO using the Bioconductor package GEOquery. An additional quantile normalization step was included if the data required further normalization. For the RNA-Seq analysis, data was normalized using the Voom function in the Limma package which converts read counts to weighted log base 2 counts per million. For both the meta-analysis and RNA-Seq analyses, data was summarized using the linear model in the Limma package.

Gene Signature Definition and Analysis.

Endotoxin Tolerance and Inflammatory gene signatures were derived from previously published [Pena et al 2011] microarray analyses of human PBMC identifying differentially expressed genes compared to control PBMCs. To enable more direct comparisons between signatures, differentially expressed inflammatory genes were further reduced from 178 to 93 genes using an experimental endotoxaemia microarray dataset (GSE3284) obtained from the PBMC of healthy individuals stimulated in vivo with low-dose LPS for 2 and 6 hours. Importantly the two primary gene expression datasets (GSE22248 & GSE3284) used to derive signatures were then excluded from subsequent gene-set validation tests. Analysis of the presence or absence of the Endotoxin Tolerance and Inflammatory signatures in patients and controls was performed using the well-established, statistically-rigorous gene set test ROAST. Gene set tests essentially ask whether a given gene set/signature is signature enriched in a dataset. The ROAST method additionally allows for the consideration of a gene's direction of expression when calculating the enrichment, which increases the accuracy of the test in cases where the direction of the gene's expression is known (Wu et al., Bioinformatics, 20101 26(17):2176-82). ROAST was run with 99999 rotations and so the most significant p-value resulting from this test is 0.00001. Additional endotoxin tolerance-related signatures were also defined at multiple significance cut-offs from the previously published dataset (FIG. 4) and from an alternate, independent endotoxin tolerance dataset [Del Fresno C, et al. Journal of Immunology 2009; 182:6494-507] from cystic fibrosis patients with essentially identical results.

Random Forest Analysis of Diagnostic Predictions.

Each dataset was split into training (containing 75% of sepsis patients and controls) and test (containing 25% of sepsis patients and controls) sets using random sampling. Datasets GSE13015 and GSE11755 were omitted from this analysis due to low numbers of controls (N=3) in each dataset. For each of the remaining 8 datasets, the model was defined on the training set and then assessed on the test set using the randomForest package [Liaw A, Wiener M. R News 2002; 2:18-22] with ntree set to 1000. The procedure was repeated 100 limes, and the average prediction accuracies recorded for each data set.

Example 1: Definition and Characterization of the Signature

Figure 2:
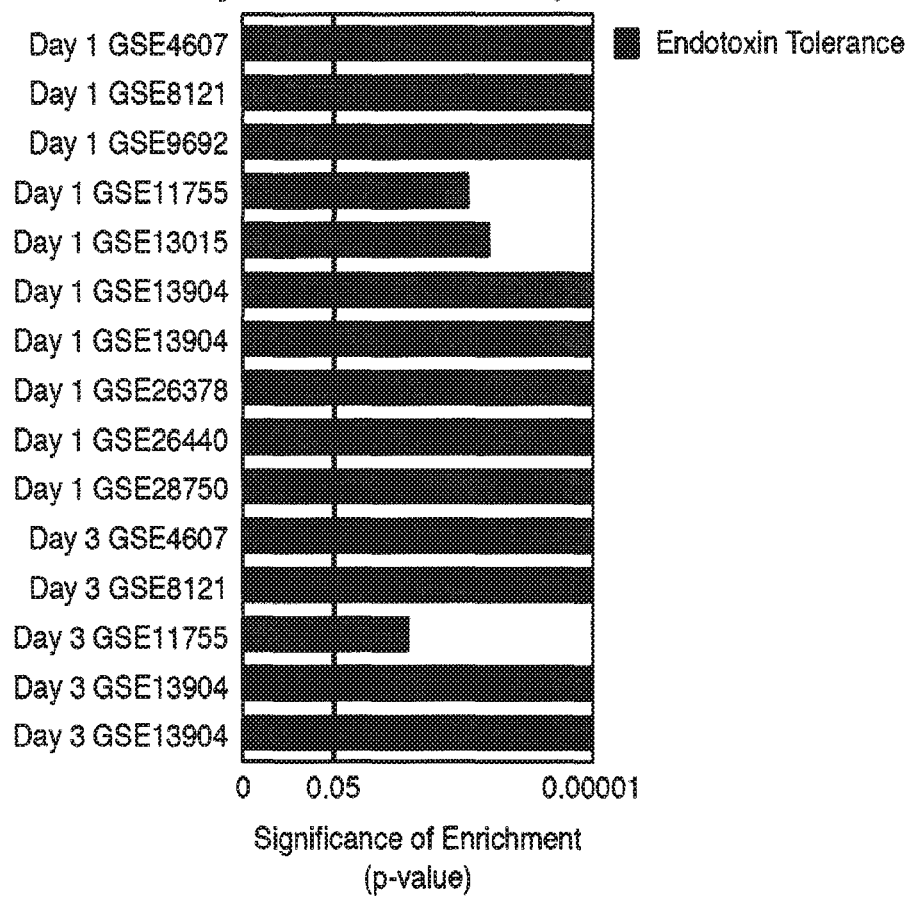
FIG. 2 demonstrates that reanalysis of differential gene expression from sepsis patients from published datasets showed a strong association with the Endotoxin Tolerance Signature. A gene-set test approach, ROAST, was used to characterize the enrichment of "Endotoxin Tolerance" in sepsis patients versus controls from 9 previously published datasets. All datasets contained sepsis patients recruited at day 1 or 3 post-ICU admission and were compared to "healthy" controls. The ROAST gene-set test was run with 99999 rotations so the most significant p-value resulting from this test is 0.00001. P-values from the ROAST gene-set test were graphed as log (1/p-value), but the untransformed p-values are shown for ease of visualization.
Figure 3:
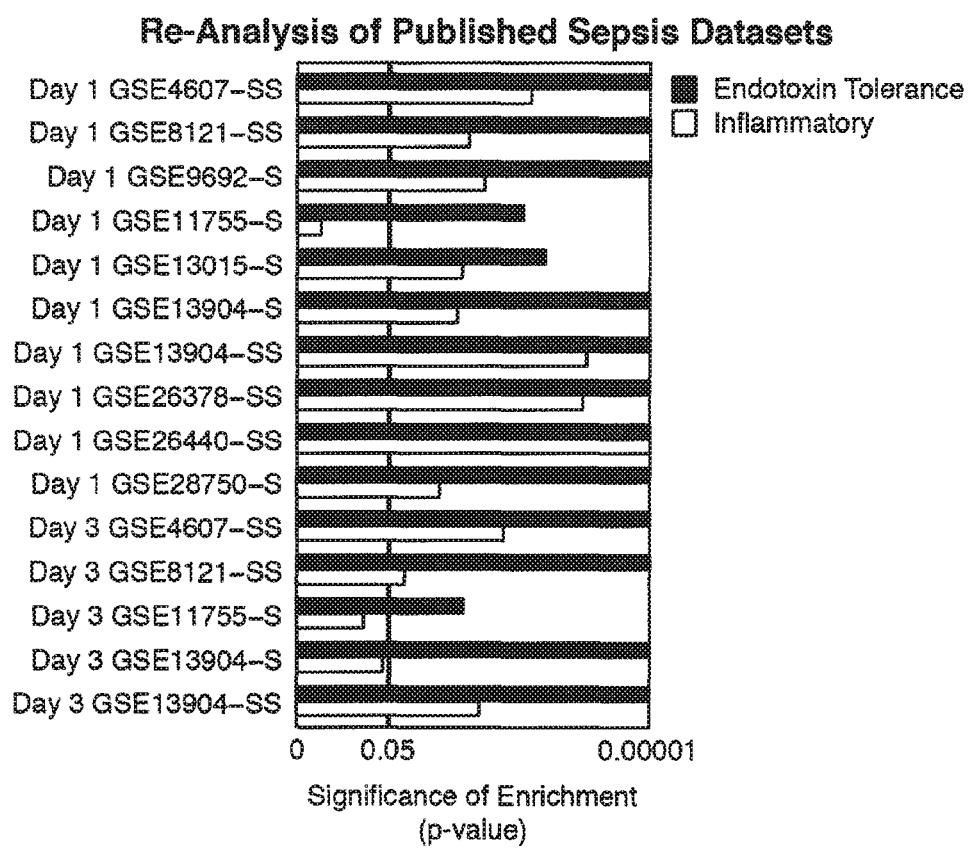
FIG. 3 shows that sepsis patients based on published datasets generally showed a less significant association with the Inflammatory Signature. A gene-set test approach, ROAST, was used to characterize the enrichment of Inflammatory signature (white) relative to the Endotoxin Tolerance Signature (grey) in sepsis patients cf. controls in 9 previously published datasets. All datasets contained sepsis patients recruited at days 1 and/or 3 post-ICU admission and were compared to 'healthy' controls. The ROAST gene-set test was run with 99999 rotations so the most significant p-value resulting from this test is 0.00001. P-values from the ROAST gene-set test were graphed as log (1/p-value), but the untransformed p-values are shown for ease of visualization.
Figure 4:
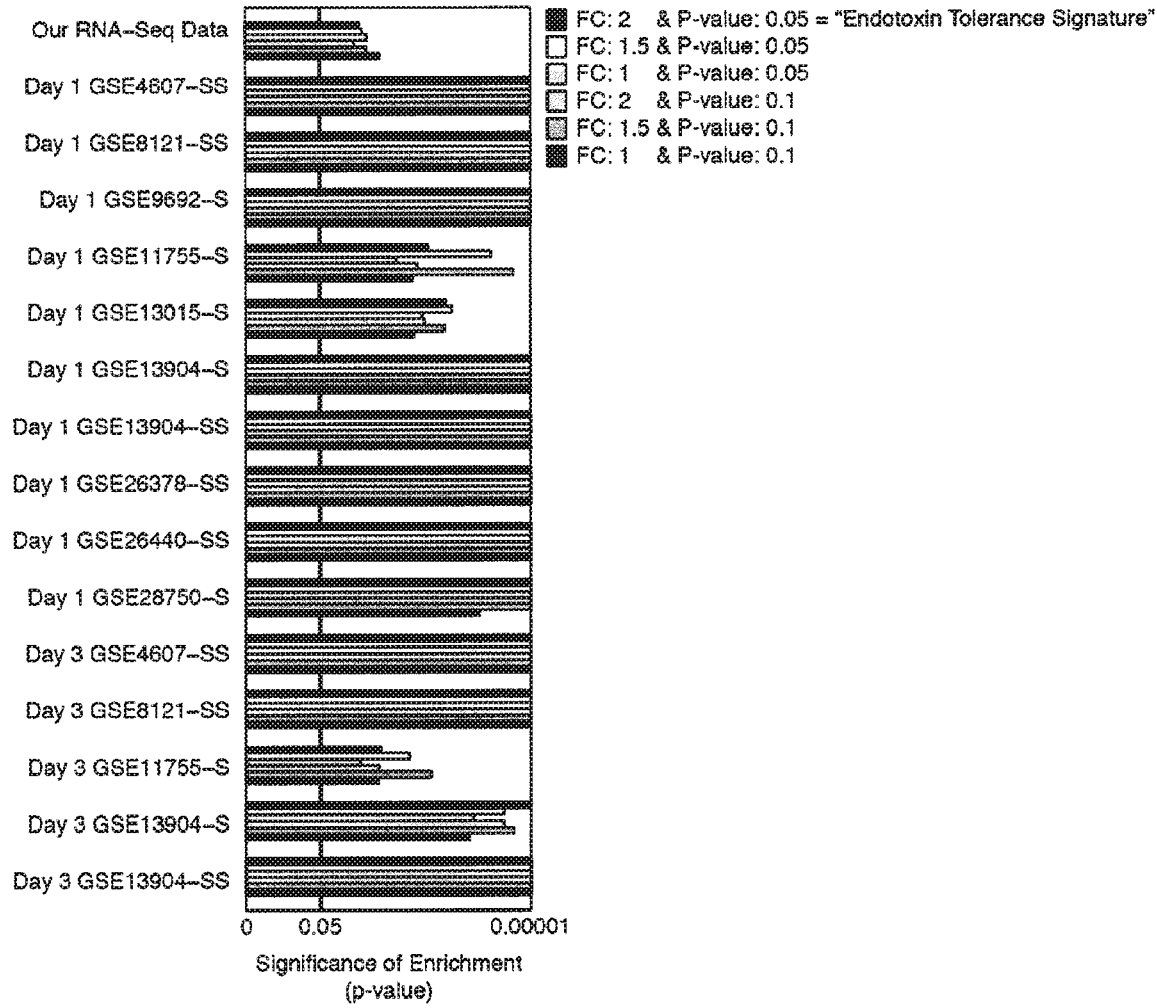
FIG. 4 reveals that the association between endotoxin tolerance and sepsis is independent of the specific method used to define the Endotoxin Tolerance Signature. Different endotoxin tolerance related-signatures were identified based on genes uniquely differentially expressed in endotoxin-tolerant PBMCs, but not inflammatory PBMCs, as compared to controls at various fold-change (FC) and P-value cut-offs. Datasets were as described in the legend to FIG. 3 except the Day 0 RNA-Seq dataset is the one described here. The final Endotoxin Tolerance Signature was defined at fold-change (FC) and P-value cut-offs of 2 and 0.05, respectively.

Confirmed Sepsis patients express an "Endotoxin Tolerance Signature." To characterize the development of the immunosuppressive stage in sepsis and to conclusively determine its links with endotoxin tolerance, a robust bioinformatics approach was taken. To define an endotoxin tolerance gene signature, microarray analyses of human peripheral blood mononuclear cells (PBMC) treated either once with LPS to model inflammatory signalling, or twice to model endotoxin tolerance was used. An "Endotoxin Tolerance Signature" (Table A below), comprising 99 genes was identified based on genes uniquely differentially expressed in endotoxin-tolerant PBMCs, but not inflammatory PBMCs, as compared to controls. For comparison, we defined an "Inflammatory Signature" from previous PBMC microarray data (Pena et al., 2011) and an in vivo experimental endotoxemia dataset (Calvano et al., 2005) (FIG. 1, Table 4). Having defined a genetic signature for endotoxin tolerance, we performed a global meta-analysis on 9 published, independent and blinded clinical sepsis cohorts, encompassing 536 early sepsis patients (1 or 3 days post-ICU admission) and 142 healthy controls (Table 2; FIGS. 2, 3, 4). In all of these reanalyzed datasets, patients had been recruited at either 1 or 3 days post-ICU admission.

TABLE A

Endotoxin Tolerance Signature Genes and Their Relative Expression in Endotoxin Tolerant PBMCs vs. Controls

| Gene Symbol | Description | Fold Change |
| --- | --- | --- |
| ADAM15 | ADAM metallopeptidase domain 15 | −2.1 |
| ADAMDEC1 | ADAM-like, decysin 1 | 3.0 |
| ALCAM | Activated leukocyte cell adhesion molecule | −2.0 |
| ALDH1A1 | Aldehyde dehydrogenase 1 family, member A1 | −3.8 |
| ANKRD1 | Ankyrin repeat domain 1 (cardiac muscle) | 4.1 |
| C19orf59 | Chromosome 19 open reading frame 59 | 12.6 |
| CA12 | Carbonic anhydrase XII | 8.2 |
| CAMP | Cathelicidin antimicrobial peptide | −3.9 |
| CCL1 | Chemokine (C-C motif) ligand 1; SCYA1 | 7.1 |
| CCL19 | Chemokine (C-C motif) ligand 19; MIP3β | 4.1 |
| CCL22 | Chemokine (C-C motif) ligand 22; MDC | 7.0 |
| CCL24 | Chemokine (C-C motif) ligand 24; Eotaxin-2 | 19.8 |
| CCL7 | Chemokine (C-C motif) ligand 7 | 21.0 |
| CD14 | CD14 molecule | 2.5 |
| CD300LF | CD300 molecule-like family member F | 2.1 |
| CD93 | CD93 molecule | 4.6 |
| CDK5RAP2 | CDK5 regulatory subunit associated protein 2 | 2.2 |
| CPVL | Carboxypeptidase, Vitellogenic-like | −3.6 |
| CST3 | Cystatin C | −4.2 |
| CST6 | Cystatin E/M | −2.5 |
| CTSK | Cathepsin K | −2.4 |
| CXCL10 | Chemokine (C-X-C motif) ligand 10 | −9.9 |
| CYP1B1 | Cytochrome P450, family 1, subfamily B, polypeptide 1 | 2.1 |
| CYP27B1 | Cytochrome P450, family 27, subfamily B, polypeptide 1 | 3.0 |
| DDIT4 | DNA-damage-inducible transcript 4 | 2.2 |
| DHRS9 | Dehydrogenase/reductase (SDR family) member 9 | −5.7 |
| DPYSL3 | Dihydropyrimidinase-like 3 | 2.6 |
| EGR2 | Early growth response 2 | 2.0 |
| EMR1 | EGF-like module containing, mucin-like, hormone receptor-like 1 | 2.1 |
| EMR3 | EGF-like module containing, mucin-like, hormone receptor-like 3 | 2.4 |
| FBP1 | Fructose-1,6-bisphosphatase 1 | 3.2 |
| FCER1G | Fc fragment of IgE, high affinity I, receptor for; gamma polypeptide | 2.0 |
| FCER2 | Fc fragment of Ige, low affinity II, receptor for (CD23) | 2.9 |
| FPR1 | Formyl peptide receptor 1 | 5.7 |
| FPR2 | Formyl peptide receptor 2 | 4.9 |
| GK | Glycerol kinase | 2.3 |
| GPNMB | Glycoprotein (transmembrane) NMB | −8.1 |
| GPR137B | G protein-coupled receptor 137B | 2.2 |
| HBEGF | Heparin-binding EGF-like growth factor | 2.5 |
| HIST1H1C | Histone cluster 1, H1C | 2.3 |
| HIST2H2AA3 | Histone cluster 2, H2AA3 | 4.0 |

TABLE A-continued

Endotoxin Tolerance Signature Genes and Their Relative Expression in Endotoxin Tolerant PBMCs vs. Controls

| Gene Symbol | Description | Fold Change |
|---|---|---|
| HIST2H2AC | Histone cluster 2, H2AC | 3.6 |
| HK2 | Hexokinase 2 | 2.4 |
| HK3 | Hexokinase 3 (white cell) | 2.1 |
| HPSE | Heparanase | 2.4 |
| HSD11B1 | Hydroxysteroid (11-beta) dehydrogenase 1 | 4.1 |
| HTRA1 | HTRA serine peptidase 1 | −3.3 |
| IL18BP | Interleukin 18 binding protein | −3.5 |
| IL3RA | Interleukin 3 receptor, alpha (low affinity) | 4.2 |
| ITGB8 | Integrin, beta 8 | 2.1 |
| KIAA1199 | KIAA1199 | 4.1 |
| LILRA3 | Leukocyte immunoglobulin-like receptor, subfamily A (without TM domain), member 3 | 14.0 |
| LILRA5 | Leukocyte immunoglobulin-like receptor, subfamily A (with TM domain), member 5 | 2.6 |
| LIPA | Lipase A, lysosomal acid, cholesterol esterase | −4.5 |
| LY86 | Lymphocyte antigen 86 | −2.6 |
| MARCO | Macrophage receptor with collagenous structure | 3.7 |
| MGST1 | Microsomal glutathione S-transferase 1 | 2.7 |
| MMP7 | Matrix metallopeptidase 7 (matrilysin, uterine) | 12.0 |
| MT1F | Metallothionein 1F | 16.2 |
| MT1G | Metallothionein 1G | 61.1 |
| MT1H | Metallothionein 1H | 51.1 |
| MT1M | Metallothionein 1M | 23.8 |
| MT1X | Metallothionein 1X | 14.8 |
| MXD1 | MAX dimerization protein 1 | 2.0 |
| MYADM | Myeloid-associated differentiation marker | 2.1 |
| NEFH | Neurofilament, heavy polypeptide | 2.1 |
| NQO1 | NAD(P)H dehydrogenase, Quinone 1 | −2.3 |
| NRIP3 | Nuclear receptor interacting protein 3 | 2.2 |
| OLIG2 | Oligodendrocyte lineage transcription factor 2 | 2.5 |
| PANX2 | Pannexin 2 | 2.7 |
| PAPLN | Papilin, proteoglycan-like sulfated glycoprotein | 2.0 |
| PDLIM7 | PDZ and LIM domain 7 (enigma) | 3.1 |
| PLAUR | Plasminogen activator, Urokinase receptor | 2.7 |
| PLD3 | Phospholipase D family, member 3 | −3.1 |
| PPBP | Pro-platelet basic protein (chemokine (C-X-C motif) ligand 7) | 6.8 |
| PROCR | Protein C receptor, endothelial | 2.0 |
| PSTPIP2 | Proline-serine-threonine phosphatase interacting protein 2 | −2.1 |
| PTGES | Prostaglandin E synthase | 3.3 |
| PTGR1 | Prostaglandin reductase 1 | 2.6 |
| RAB13 | RAB13, member RAS oncogene family | 2.3 |
| RARRES1 | Retinoic acid receptor responder (Tazarotene induced) 1 | −3.8 |
| RETN | Resistin | 4.4 |
| RHBDD2 | Rhomboid domain containing 2 | 2.9 |
| RNASE1 | Ribonuclease, RNAse A family, 1 (pancreatic) | −10.4 |
| S100A12 | S100 calcium binding protein A12 | 3.7 |
| S100A4 | S100 calcium binding protein A4 | −2.7 |
| S100A8 | S100 calcium binding protein A8 | 2.1 |
| S100A9 | S100 calcium binding protein A9 | 2.5 |
| SERPINA1 | Serpin peptidase inhibitor, Clade A (α-1 anti-proteinase, anti-trypsin), member 1 | 5.7 |
| SERPINB7 | Serpin peptidase inhibitor, Clade B (ovalbumin), member 7 | 4.3 |
| SLC16A10 | Solute carrier family 16, member 10 (aromatic amino acid transporter) | 2.9 |
| SLC7A11 | Solute carrier family 7 (anionic amino acid transporter light chain, xc-system), member 11 | 2.3 |
| TGM2 | Transglutaminase 2 | 2.1 |
| TLR7 | Toll-like receptor 7 | −2.2 |
| TMEM158 | Transmembrane protein 158 (gene/pseudogene) | 2.1 |
| TREM1 | Triggering receptor expressed on myeloid cells 1 | 3.5 |
| TSPAN4 | Tetraspanin 4 | −2.4 |
| UPP1 | Uridine phosphorylase 1 | 2.1 |
| VCAN | Versican | 5.3 |

TABLE 4

Inflammatory Signature Genes and Their Relative Expression in Inflammatory PBMCs vs Controls

| Gene Symbol | Description | Fold Change |
|---|---|---|
| CCL20 | Chemokine (C-C motif) ligand 20; MIP3α | 14.6 |
| CCL3L1 | Chemokine (C-C motif) ligand 3-like 1; MIP1AP | 9.2 |
| G0S2 | G0/G1switch 2 | 7.2 |
| CFB | Complement factor 9 | 6.1 |
| AK4 | Adenylate kinase 4 | 5.4 |
| IFIT3 | Interferon-induced protein with tetratricopeptide repeats 3 | 5.1 |
| HERC5 | HECT and RLD domain containing E3 ubiquitin protein ligase 5 | 4.8 |
| PDSS1 | Prenyl (decaprenyl) diphosphate synthase, Subunit 1 | 4.8 |
| BATF | Basic leucine zipper transcription factor, ATF-1ike | 4.7 |
| DNAAF1 | Dynein, axonemal, assembly factor 1 | 4.7 |
| XAF1 | XIAP associated factor 1 | 4.4 |
| PIM2 | PIM-2 oncogene | 4.2 |
| IFI44 | Interferon-induced protein 44 | 3.7 |
| F3 | Coagulation factor III (thromboplastin, tissue factor) | 3.6 |
| FAM129A | Family with sequence similarity 129, member A | 3.5 |
| IFIT2 | Interferon-induced protein with tetratricopeptide repeats 2 | 3.4 |
| KCNJ2 | Potassium inwardly-rectifying channel, subfamily J, member 2 | 3.4 |

TABLE 4-continued

Inflammatory Signature Genes and Their Relative Expression in Inflammatory PBMCs vs Controls

| Gene Symbol | Description | Fold Change |
|---|---|---|
| MX2 | Myxovirus (influenza virus) resistance 2 (mouse) | 3.4 |
| EIF2AK2 | Eukaryotic translation initiation factor 2-alpha kinase 2 | 3.2 |
| CCL3L3 | Chemokine (C-C motif) ligand 3-like 3; LD78 | 3.1 |
| IRF7 | Interferon regulatory factor 7 | 3.1 |
| CXCL2 | Chemokine (C-X-C motif) ligand 2; MIP2α | 3.0 |
| FFAR2 | Free fatty acid receptor 2 | 3.0 |
| RIPK2 | Receptor-interacting serine-threonine kinase 2 | 3.0 |
| ADORA2A | Adenosine A2a receptor | 2.9 |
| SAMD9L | Sterile alpha motif domain containing 9-like | 2.9 |
| GRAMD1A | GRAM domain containing 1A | 2.8 |
| SOD2 | Superoxide dismutase 2, mitochondrial | 2.8 |
| SOCS1 | Suppressor of cytokine signaling 1 | 2.7 |
| CD80 | CD80 molecule | 2.6 |
| TNF | Tumor necrosis factor | 2.6 |
| CASP5 | Caspase 5, apoptosis-related cysteine peptidase | 2.5 |
| CD83 | CD83 molecule | 2.5 |
| IFI35 | Interferon-induced protein 35 | 2.5 |
| PIM1 | Pim-1 oncogene | 2.5 |
| SLAMF7 | SLAM family member 7 | 2.5 |
| TRIM25 | Tripartite motif containing 25 | 2.5 |
| C1orf122 | Chromosome 1 open reading frame 122 | 2.4 |
| GBP4 | Guanylate binding protein 4 | 2.4 |
| PIM3 | Pim-3 oncogene | 2.4 |
| GBP2 | Guanylate binding protein 2, interferon-inducible | 2.3 |
| RNF144B | Ring finger protein 144B | 2.3 |
| TXN | Thioredoxin | 2.3 |
| YRDC | Yrdc domain containing (*E. Coli*) | 2.3 |
| ALCAM | Activated leukocyte cell adhesion molecule | 2.2 |
| ANTXR2 | Anthrax toxin receptor 2 | 2.2 |
| ISG20 | Interferon stimulated exonuclease gene 20 kda | 2.2 |
| OASL | 2'-5'-oligoadenylate synthetase-like | 2.2 |
| PARP9 | Poly (ADP-ribose) polymerase family, member 9 | 2.2 |
| PTX3 | Pentraxin 3, long | 2.2 |
| TNFAIP2 | Tumor necrosis factor, alpha-induced protein 2 | 2.2 |
| TNFSF10 | Tumor necrosis factor (ligand) superfamily, member 10 | 2.2 |
| B4GALT5 | UDP-Gal:betaglenac beta 1,4-galactosyltransferase, polypeptide 5 | 2.1 |
| BCL3 | B-cell CLL/lymphoma 3 | 2.1 |
| EDN1 | Endothelin 1 | 2.1 |
| GADD45B | Growth arrest and DNA-damage-inducible, beta | 2.1 |
| IRAK2 | Interleukin-1 receptor-associated kinase 2 | 2.1 |
| JUNB | Jun B proto-oncogene | 2.1 |
| MTF1 | Metal-regulatory transcription factor 1 | 2.1 |
| NFKB2 | Nuclear factor of kappa light polypeptide gene enhancer in B-cells 2 | 2.1 |
| SAMD9 | Sterile alpha motif domain containing 9 | 2.1 |
| UPB1 | Ureidopropionase, beta | 2.1 |
| GCH1 | GTP cyclohydrolase 1 | 2.0 |
| HSH2D | Hematopoietic SH2 domain containing | 2.0 |
| NFKBIZ | Nuclear factor of kappa light polypeptide gene enhancer in B-cells inhibitor, zeta | 2.0 |
| TNIP1 | TNFAIP3 interacting protein 1 | 2.0 |
| ZC3H12A | Zinc finger CCCH-type containing 12A | 2.0 |
| CORO1B | Coronin, actin binding protein, 1B | −2.0 |
| H2AFY | H2A histone family, member Y | −2.0 |
| IFFO1 | Intermediate filament family orphan 1 | −2.0 |
| SPIRE1 | Spire homolog 1 (*Drosophila*) | −2.0 |
| TSC22D3 | TSC22 domain family, member 3 | −2.0 |
| CSF1R | Colony stimulating factor 1 receptor | −2.1 |
| PLIN2 | Perilipin 2 | −2.1 |
| ZMIZ1 | Zinc finger, MIZ-type containing 1 | −2.1 |
| CTSB | Cathepsin B | −2.2 |
| LPAR6 | Lysophosphatidic acid receptor 6 | −2.2 |
| MS4A7 | Membrane-spanning 4-domains, subfamily A, member 7 | −2.2 |
| SLAMF8 | SLAM family member 8 | −2.2 |
| IDH1 | Isocitrate dehydrogenase 1 (NADP+), soluble | −2.3 |
| LTA4H | Leukotriene A4 hydrolase | −2.4 |
| CAMK1 | Calcium/calmodulin-dependent protein kinase I | −2.5 |
| CORO1C | Coronin, actin binding protein, 1C | −2.5 |
| CLEC10A | C-type lectin domain family 10, member A | −2.9 |
| CD86 | CD86 molecule | −3.1 |
| PDK4 | Pyruvate dehydrogenase kinase, isozyme 4 | −3.1 |
| ACP5 | Acid phosphatase 5, tartrate resistant | −3.2 |
| HAVCR2 | Hepatitis A virus cellular receptor 2 | −3.2 |
| ASGR1 | Asialoglycoprotein receptor 1 | −3.4 |
| NCEH1 | Neutral cholesterol ester hydrolase 1 | −3.6 |
| RCBTB2 | Regulator chromosome condensation (RCC1) & BTB (POZ) domain 2 | −3.9 |
| ADAP2 | ArfGAP with dual PH domains 2 | −4.6 |
| HMOX1 | Heme oxygenase (decycling) 1 | −5.5 |

To assess the relative expression of the Endotoxin Tolerance and Inflammatory signatures in sepsis patients versus healthy controls, a gene-set test approach was used, which examines whether a given signature (gene-set) is significantly enriched between groups in a dataset. Sepsis patients in all 9 cohorts were found to show an immunological expression profile strongly associated with the Endotoxin Tolerance Signature when compared to controls (FIG. 2). These results were independent of the fold-change/statistical cut-offs used to define the Endotoxin Tolerance Signature (FIG. 4). While the Inflammatory Signature was significantly associated with most of the datasets, this association was consistently weaker than for the Endotoxin Tolerance Signature (FIG. 3). In contrast to previous reports associating endotoxin tolerance only with late stage sepsis (Cavaillon J, C Adrie, C Fitting, M Adib-Conquy. J Endotoxin Res 2005; 11:311-320; Otto, G P, M Sossdorf, R A Claus, J Rodel, K Menge, K Reinhart, M Bauer, N C Riedemann. Critical Care 2011; 15:R183; Schefold J C, D Hasper, H D Volk, PReinke. Medical hypotheses 2008; 71:203-208), the association with the "Endotoxin Tolerance Signature" was present in sepsis patients as early as Day 1 post-ICU admission, and was maintained on Day 3, consistent with the early development of a "stable" endotoxin tolerance profile in sepsis patients (FIG. 2). Thus the immune dysfunction in sepsis appears to be characterized by endotoxin tolerance.

The "Endotoxin Tolerance Signature" Develops Very Early in Patients with Sepsis and is Detectable Before Diagnosis.

One limitation of all 9 previously published datasets used in the prior meta-analysis was the analysis of the sepsis patient transcriptome following "confirmed diagnosis" of sepsis and not at first presentation. Accordingly a unique cohort of patients at the earliest possible stage of clinical disease was generated to better understand the timing of endotoxin tolerance development and the diagnostic utility of the signature identified herein. Patients were recruited immediately after clinical suspicion of sepsis, based on the attending physician's analysis of patient history, physical examination and stat request for microbial culture testing. RNA-Seq was performed on RNA isolated from the initial blood sample taken for cultures to aid in sepsis diagnosis/microbial identification. An appropriate power calculation was performed and based on this, 72 very early suspected sepsis patients (Table 3) were recruited, as well as an additional 11 control patients who were recruited prior to elective surgery with no underlying morbidities. Investigating the potential for an early means of differential diagnosis in this clinically challenging cohort of patients who initially presented with variable serious derangements in physiology (potentially caused by sepsis) has major clinical implications.

Based on the earliest recorded clinical assessments following sample isolation (Table 3), patients in the cohort of 72 suspected sepsis patients were retrospectively classified as "Sepsis" (n=37), or "No Sepsis" (n=35), consistent with current sepsis diagnostic criteria (R. C. Bone, et al., 2009). Strikingly, even at the earliest stage of clinical sepsis, the Endotoxin Tolerance Signature was significantly enriched only in patients who were subsequently confirmed to have sepsis and not those with other diagnoses ("No Sepsis"), as compared with healthy controls (FIG. 5A). When combined with the results from the prior meta-analysis, sepsis appears to be strongly associated with endotoxin tolerance throughout all initial stages of clinical disease (FIGS. 2 & 5A). Additionally, while the Inflammatory Signature did not reach statistical significance in the "No Sepsis" group, the contrasting relative enrichment of the Endotoxin Tolerance and Inflammatory Signatures in the 2 groups may indicate a fundamental difference in the balance of endotoxin tolerance and inflammation unique to sepsis patients. Finally, the Endotoxin Tolerance Signature was also enriched in the "Sepsis" group when directly compared to the "No Sepsis" group (FIG. 5B), which supports the specificity of endotoxin tolerance to sepsis and not just to "ill" patients.

One of the challenges in diagnosing sepsis is the confirmation of infection due to the low sensitivity of bacterial cultures (R C Bone, et al., 2009). Indeed the current sepsis diagnostic criteria are based on "suspected infection," rather than confirmed infection due to these sensitivity issues (R C Bone, et al., 2009). This concept was highlighted by comparing signature enrichment with microbial culture results in both the patient groups. In agreement with previous results, the Endotoxin Tolerance Signature was higher in the "Sepsis group" (FIG. 5C) and the Inflammatory Signature in the "No Sepsis" group regardless of the microbial culture result (FIG. 5D), further highlighting the interesting inverse trend of the signatures among these two groups of "ill" patients. As expected, given the sensitivity issues of microbial cultures, while the Endotoxin Tolerance Signature showed more significant enrichment in the culture positive group, there was also strong enrichment in the culture negative group, consistent with the presence of possibly incorrectly identified "infection negative" patients in this group (FIG. 5C). As the RNA-Seq analysis was performed on the same blood samples used for diagnostic microbial cultures, the strong association between sepsis and the Endotoxin Tolerance Signature, suggests the Endotoxin Tolerance Signature may provide a more sensitive tool for diagnostics than microbial culture.

Together these data show that endotoxin tolerance is present throughout the initial clinical course of sepsis, detectable before "diagnosis," and can be used to differentiate patients who develop sepsis in a cohort of patients where there was a suspicion of sepsis.

TABLE 5

Statistics regarding Organ Failure and Sites of Infection in the Cohort of Patients

|  | Number of Patients |
|---|---|
| A. Site of Organ Failure | |
| Lung (Respiratory Failure) | 22 |
| Kidney (Acute Kidney Injury) | 41 |
| Liver | 9 |
| Cardiovascular System | 22 |
| B. Site of Infections | |
| Blood | 9 |
| Urinary Tract | 10 |
| Respiratory Tract | 6 |
| Gastrointestinal Tract | 4 |
| Skin and Soft Tissues | 3 |
| Bone | 1 |

Next, the relevance of the endotoxin tolerance-driven immunosuppressive state (as detected by the Endotoxin Tolerance Signature) to the severity of sepsis as defined by the subsequent development of organ dysfunction in the suspected sepsis patient cohort was investigated. Subsequent organ dysfunction development was assessed within 48 hours of study enrolment (cardiovascular, coagulation, kidney, liver, and respiratory; Tables 4 & 5) with patients retrospectively grouped into organ-dysfunction positive and negative groups, independent of sepsis diagnosis. These groups were then subjected to the same gene-set test analysis as above. Interestingly, the Endotoxin Tolerance Signature was found to be significantly associated with the development of individual or multiple (3+) organ dysfunction (FIG. 6A; except coagulation failure). Although ICU admission may depend on the inherent subjectivity of hospital regulations, such as space or number of beds available in each department, patients that are moved to the ICU are generally in a deteriorating condition with an increased risk of mortality. Therefore, the requirement for ICU admission was also assessed as a second, less precise measure of disease severity and showed that the Endotoxin Tolerance Signature was again associated with increased disease severity (FIG. 6B). These results indicate that endotoxin tolerance is associated with sepsis severity and specifically the subsequent development of organ failure.

Figure 7:
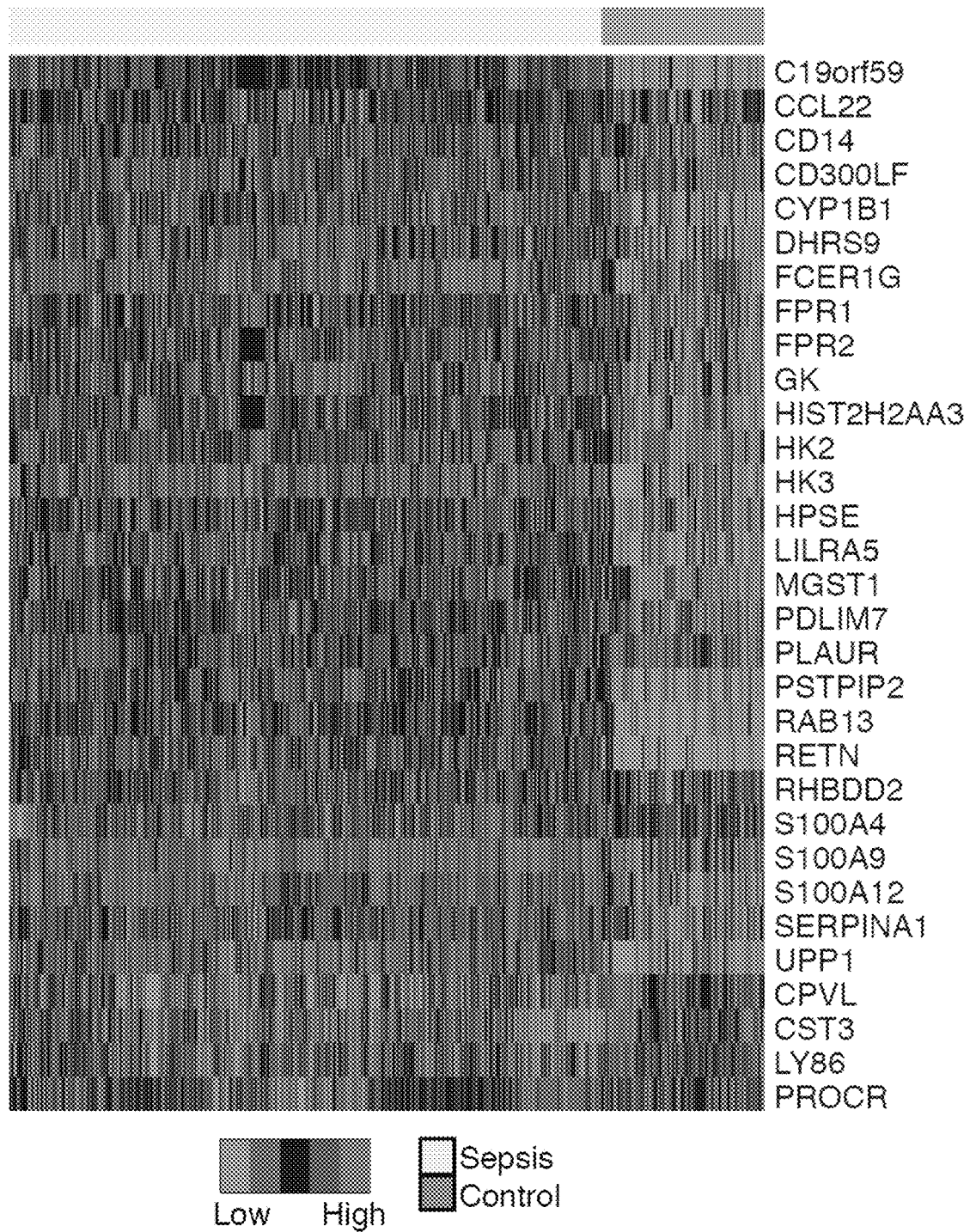
FIG. 7 shows a core set of endotoxin tolerance genes characteristic of sepsis patients. A core set of 31 of the 99 genes from the Endotoxin Tolerance Signature was determined based on the most frequently differentially expressed genes observed in all sepsis patient studies (literature and in-house datasets). For better visual comparison across different studies, each individual dataset was further transformed by dividing gene expression values into six equal bins. Data is presented as a heatmap with lightest and darkest shading representing relatively large and relatively small changes in expression, respectively. The differentiation was more obvious as a color heatmap.

Given the strong association between endotoxin tolerance and sepsis across more than 600 patients from 10 independent datasets, the utility of the Endotoxin Tolerance Signature as a tool in sepsis diagnosis was investigated. While the full 99 gene, Endotoxin Tolerance Signature was useful for characterizing the immune dysfunction in sepsis, a smaller number of genes is of more use in a diagnostic test. Thus, the 99-gene signature was further analysed to identify useful subsets of this initial signature that could subsequently tested for diagnostic utility. To do this, genes that showed greater than 1.5 fold differential expression between sepsis patients and controls across the majority (7+) of the 9 literature datasets were selected. This identified a subset of 31 genes from the original 99-gene Endotoxin Tolerance Signature (FIG. 7).

The classification algorithm randomForest was used to assess the ability of the genes in the identified 31-gene subset to classify sepsis patients from controls. Each dataset (external and internal) was divided into training and test sets and randomForest classification was performed independently on each dataset. The 31-gene subset showed excellent accuracy when separating sepsis patients from controls with an average accuracy of 95.7% across all datasets (Table 6). The 31-gene subset also showed strong performance in predicting sepsis and individual/combined organ failure in a group of patients with a suspicion of sepsis, with accuracies ranging from 62.4-87.4% (Table 6). This same analysis was also performed using the full 99-gene Endotoxin Tolerance Signature, and this gene set was found to provide equivalent performance supporting the suitability of the gene reduction strategy (Table 7). Area under the curve of receiver operating characteristic (AUC) assessments performed similarly. The strong performance of the 31-gene subset across multiple distinct datasets and at a clinically relevant time-point (current time of diagnostic cultures) supports the use of the 31-gene subset in the diagnosis of sepsis. The strong association between endotoxin tolerance and sepsis was identified across 10 distinct datasets and was independent of location, method, gender, age, ethnicity, and sepsis diagnostic criteria variables. Accordingly, both the full 99-gene Endotoxin Tolerance Signature and the 31-gene subset will have utility as a tool in sepsis diagnosis. Accurate diagnostic tools for sepsis are of high clinical priority due to the importance of early intervention in sepsis and the lack of clinical features specific to sepsis [Hotchkiss R S, Monneret G, Payen D. Lancet Infectious Diseases 2013; 13: 260-8]. An additional benefit to using endotoxin tolerance-related biomarkers is that they would also provide information regarding the patients' immune functional status.

TABLE 6

Diagnostic Potential of the Endotoxin Tolerance Signature*

| Variable | Accuracy using 31-gene Endotoxin Tolerance Subset | Accuracy using 99-gene Endotoxin Tolerance Signature |
|---|---|---|
| Sepsis patient numbers in brackets vs. Controls | | |
| In-house Sepsis study (37) vs. Controls | 93.3% | 92.7% |
| GSE28750 study (30) vs. Controls | 99.3% | 97.4% |
| GSE9692 study (45) vs. Controls | 95.1% | 96.6% |
| GSE13904 study (227) vs. Controls | 96.3% | 94.2% |
| GSE26440 study (130) vs. Controls | 96.3% | 96.0% |
| GSE4607 study (84) vs. Controls | 93.6% | 92.6% |
| GSE8121 study (71) vs. Controls | 93.2% | 92.2% |
| GSE26378 study (70) vs. Controls | 98.3% | 98.6% |
| Mean | 95.7% | 95.0% |
| Sepsis vs. No Sepsis | | |
| Sepsis vs. No Sepsis | 62.4% | 64.2% |
| Organ Failure vs. No Organ Failure | | |
| Respiratory | 77.5% | 75.5% |
| Cardiovascular | 77.2% | 73.6% |
| Liver | 77.8% | 78.0% |
| Acute Kidney Injury | 71.5% | 74.1% |
| Coagulation | 87.4% | 86.4% |
| Combined (3+) | 77.3% | 73.7% |

Table 6 Footnotes: *Each dataset was split into training (containing ⅔ of sepsis patients and controls) and test (containing ⅓ of sepsis patients and controls) sets using random sampling. Datasets GSE13015 and GSE11755 were omitted from this analysis due to low numbers of controls (N = 3) in each dataset. For each of the remaining 8 datasets, the model was defined on the training set and then assessed on the test set using the randomForest package with ntree set to 1000. The procedure was repeated 1000 times, and the average prediction accuracies recorded for each data set. This analysis was repeated on the dataset to classify patients with an initial suspicion of sepsis who did or did not go on to develop sepsis or organ failure.

The Endotoxin Tolerance Signature showed excellent accuracy when separating sepsis patients from controls (Overall Accuracy: randomForest=95%; Area under the curve=98.9%), and demonstrated similar accuracy with individual studies containing 19-227 patients (Table 6).

The association between the Endotoxin Tolerance Signature and confirmed sepsis was strong and statistically significant in 10 distinct datasets (FIGS. 2 & 5, Table 6) and was independent of sample size, location, method, gender, age and ethnicity. These results confirm that the Endotoxin Tolerance Signature is robustly associated with very early sepsis. The Endotoxin Tolerance Signature was also associated with disease severity measured primarily by the development of organ dysfunction. Therefore, an updated model of sepsis pathogenesis mediated by an endotoxin tolerance-mediated immune dysfunction is indicated. Furthermore, the results demonstrate that immune dysfunction could be detected at a clinically relevant diagnostic time-point, providing unique information regarding the patients' functional immune status. The Endotoxin Tolerance Signature or subset could therefore help to define a subset of patients who might benefit from immunomodulation (e.g. anti-endotoxin tolerance) and supportive therapies.

Figure 5:
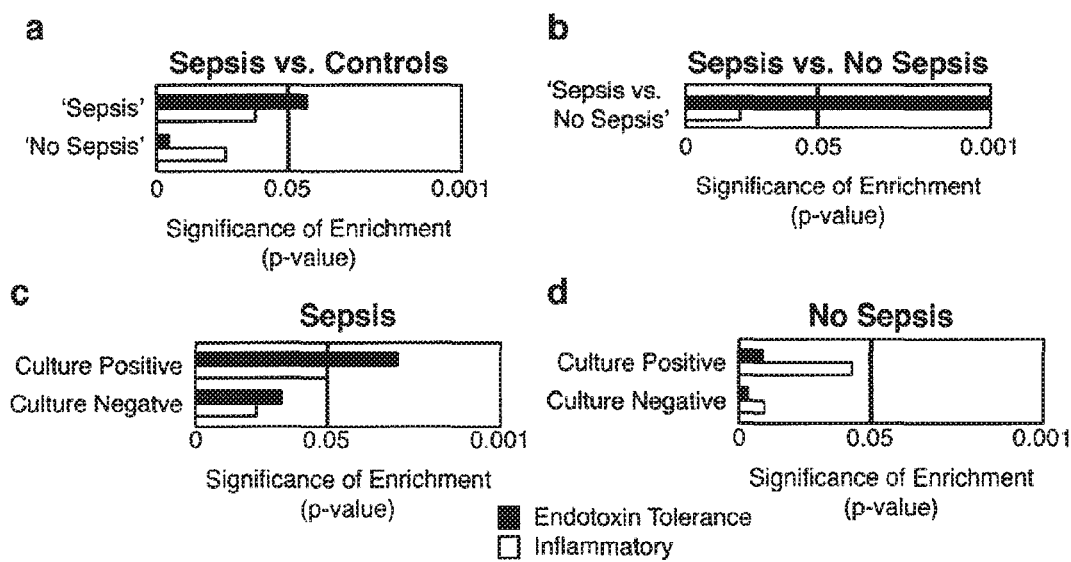
FIG. 5 shows that the Endotoxin Tolerance Signature is strongly associated with sepsis patients at first clinical presentation. A gene-set test approach was used to characterize the enrichment, cf. controls, of the Endotoxin Tolerance and Inflammatory signatures in prospective sepsis patients from a unique in-house cohort recruited on first clinical suspicion of sepsis (i.e. generally in the emergency ward prior to ICU admission). Patients groups were subsequently defined based on retrospective clinical characteristics as 'Sepsis' or 'No Sepsis' consistent with the current sepsis criteria (Table 3). Analyses were performed comparing 'sepsis' and 'no sepsis' group vs. controls (a) and 'sepsis' vs. 'no sepsis' group (b). Additionally, enrichment of the signature was also analyzed based on microbial culture results within the 'Sepsis' group (c) and the 'No Sepsis'(d) group (c).
Figure 6:
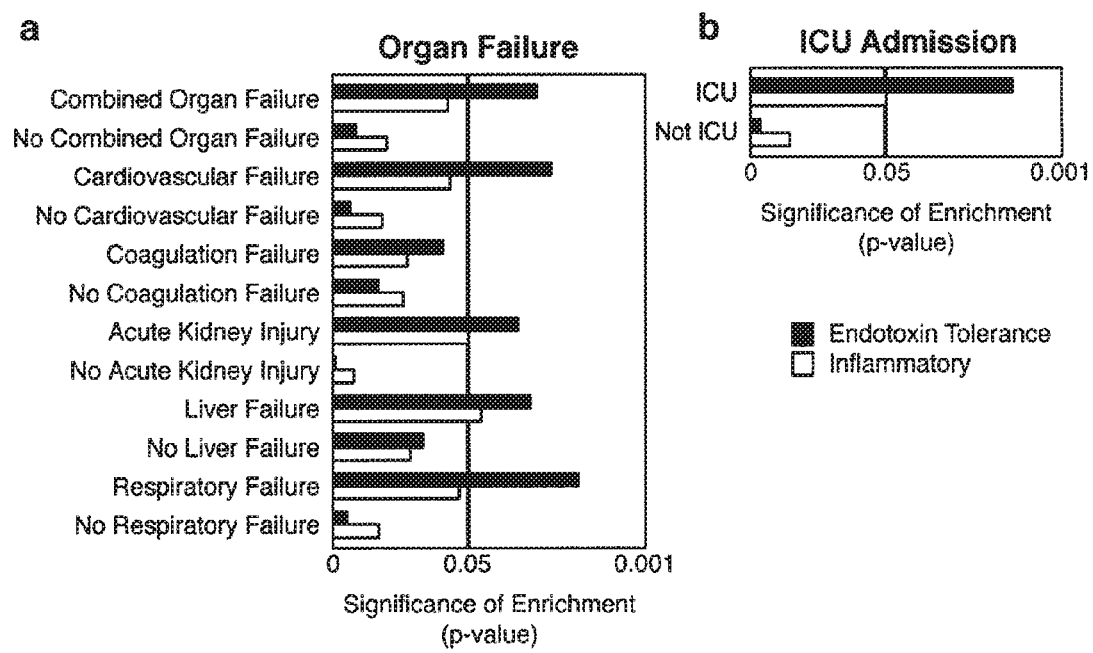
FIG. 6 shows that the Endotoxin Tolerance Signature is strongly associated with sepsis patients at first clinical presentation and is associated with the severity of the disease and organ failure. A gene-set test approach was used to characterize the enrichment, cf. surgical controls, of the Endotoxin Tolerance and Inflammatory signatures in prospective sepsis patients as described for FIG. 5. (a) Patients were grouped into individual-, combined-(3+), individual type of organ failure and no-organ failure groups, (b) Patients were grouped into those requiring and those not-requiring transfer to the ICU.

Sepsis is generally classified as an excessive inflammatory response (early stage), followed by a transition to an anti-inflammatory/immunosuppression dominated stage (Hotchkiss et al, 2013). However, the nature and timing of this later stage had not been well characterized. In contrast to previous reports associating endotoxin tolerance only with late stage sepsis, the results described herein revealed that all 10 sepsis patient cohorts showed an immunological expression profile strongly associated with the Endotoxin Tolerance Signature and subset and throughout all stages of early clinical disease (FIGS. 2, 5 & 6). From a general clinical perspective, characterizing the nature and timing of the excessive inflammatory and anti-inflammatory/immunosuppression stages is essential when considering how to treat this disease. This is especially important when different therapeutic approaches have been largely unsuccessful to date, likely due to a lack of knowledge regarding the immunological status of the patient. The data provided herein also show's that this signature was able to predict the development of sepsis, suggesting that the Endotoxin Tolerance Signature and subset have utility as a diagnostic tool.

Most importantly, this study was able to clearly demonstrate the association of the Endotoxin Tolerance Signature and subset with disease severity and organ dysfunction (FIG. 6). Organ dysfunction is considered the main factor contributing to patient deterioration and ultimately death. Importantly, the Endotoxin Tolerance Signature was present up to 48 hours prior to the development of organ dysfunction, indicating that the signature or subset can additionally be used as a screening method to assess which patients are at a higher risk for developing a worsening condition.

It is important to note that while the data indicated that the endotoxin tolerant state predominates during early sepsis, the Inflammatory Signature was also significantly enriched, albeit at relatively lower levels, in many of the comparisons performed in this study. From a biological perspective, these observations suggest that in individuals with localized infections (e.g. patients in the No Sepsis group), when an initial insult occurs, the brief inflammatory response quickly subsides to balance inflammation and bring the system to homeostasis. However, in sepsis, where there is an uncontrolled source of infection and possible contributing genetic factors (Murkin J M, and K R Walley, The Journal of Extra-Corporeal Technology 41, P43-49, 2009), the immunological balance between inflammation and endotoxin tolerance becomes detrimentally unbalanced towards a state increasingly dominated by endotoxin tolerance. The findings herein thus indicate that there is an initial (uncontrolled) infection, during which nesting immune cells, such as neutrophils and monocytes/macrophages, get activated resulting in the patient developing the first strong clinical symptoms. In septic patients, a second endotoxin stimulus likely leads to the rapid activation of an endotoxin tolerance profile. By the time of first hospital admission, this endotoxin tolerance profile predominates in peripheral blood mononuclear cells systemically, while residual neutrophilic inflammation still occurs in this rapidly turning over population.

Thus, while there remains an inflammatory component to sepsis, the endotoxin tolerance-driven state is contributing to the overall immune dysfunction in sepsis and thus the severity of the disease.

At a cellular level, the major cause of the immune dysfunction in sepsis is likely the rapid accumulation of tolerized monocytes/macrophages, locking the system into an M2-like state (Pena, O M, et al., J Immunol 2011, 186:7243-7254) in an attempt to reduce excessive neutrophilic inflammation and its consequences, such as vascular leakage, coagulation, lymphocyte death, etc. However, weakening the patient's monocyte/macrophage responses can also lead to an inability to clear the primary infection and increased susceptibility to secondary infections, despite the continued activation of other immune cell populations, such as neutrophils. Due to their continuous replenishment from the bone marrow, neutrophils are probably the main drivers of pro-inflammatory cytokine responses, although they too are likely to eventually enter an endotoxin tolerant state (Parker L C. et al., J Leukocyte Biology 2005; 78:1301-1305).

Additionally, it is demonstrated herein that the Endotoxin Tolerance Signature and subset had a higher association with positive cultures among the sepsis group, and a similar higher trend with those who had negative cultures (FIG. 5C). In contrast the Inflammatory Signature predominated among the "No Sepsis" patients with a stronger presence among those with positive cultures (FIG. 5D). It is interesting to observe the different trends among each group of patients, which are aligned with previously discussed points: An initial Inflammatory Signature that increased in the direction of negative to positive cultures in the "No Sepsis" group indicating the early increasing phase of inflammation during a possibly localized infection or an initial sterile inflammatory process. Subsequently, in patients who rapidly get extremely ill, as is the case of those patients in the "Sepsis" group, there is a rapid transition towards a systemic infection-led tolerant state, leading to a stronger and increasing presence of an endotoxin tolerant state, as observed in the described results, indicating a culture negative to culture positive trend.

Characterizing the contributions of the inflammatory and immunosuppressive programs during clinical disease is critical when considering host-directed therapies for treatment. The results described herein demonstrate that an endotoxin tolerance state predominates throughout the earliest stages of clinical sepsis and is likely driving immune dysfunction in sepsis. Thus, if there is an immunological phase characterized solely by excessive inflammation, it likely occurs pre-clinically. However, given the significant enrichment of the Inflammatory Signature in many sepsis patient groups, it is likely the combination of endotoxin tolerance and inflammation that contributes to the unique pattern of sepsis pathogenesis. These findings necessitate a shift away from a two stage model and towards a clinically relevant immune etiology characterized by endotoxin tolerance-driven immune dysfunction at the earliest stages of clinical disease. Detection of a predominant Endotoxin Tolerance Signature is supportive of the suspicion of sepsis and will, therefore, direct the treating team to consider appropriate supportive and immunomodulation therapies to balance the immune response.

In conclusion, these studies have provided the first description of a unique endotoxin tolerance profile, present very early in the course of sepsis, linked to sepsis pathogenesis, and strongly associated with the risk of organ dysfunction.

Example 2: New Therapies Based on the Endotoxin Tolerance Signature

Figure 8:
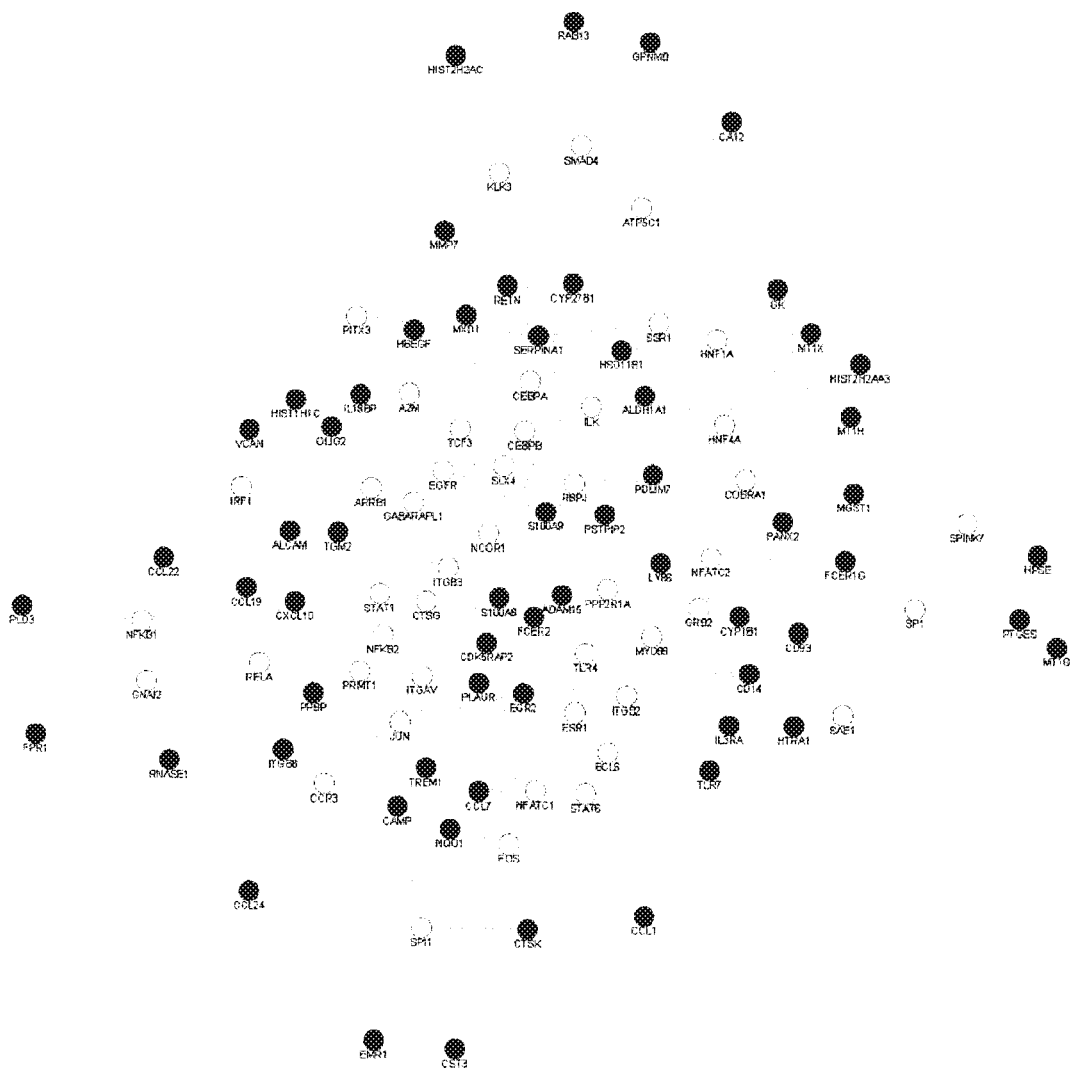
FIG. 8 demonstrates a sub-network of genes from the Endotoxin Tolerance Signature identified using the j-Activemodules plug-in of Cytoscape. First a network was created by including first level interactors of the genes listed in Table 1 and then subjected to analysis using j-Activemodules which identifies particularly dense (i.e. highly interconnected) subnetworks. Dark nodes (genes) are highly dysregulated, and light nodes are direct interactors of the dysregulated genes, lines represent "edges" and indicate experimentally proven interactions. The fact that 60 of the 99 genes in the signature were tightly interconnected in the human cell implicates a biologically meaningful relationship between these genes; i.e. that these genes are co-regulated or are involved in a common purpose in the cell. Evident within the network are hub proteins (central highly interconnected proteins involved in cellular signalling and trafficking) including Serpin A1, transcription factors CEBPα,β, EGR2, HNF4A, CXCL10, and FCER2, as well as the prominent innate immune transcription factors NFκB1, IRF1, STAT6, JUN, and FOS, and receptor TLR4 (not dysregulated themselves), suggesting their potential involvement in endotoxin tolerance.

Network analysis of the Endotoxin Tolerance genes revealed that most of the genes formed a very tight subnetwork strongly suggesting that the signature reflects critical mechanisms likely related to immune dysfunction in sepsis patients (FIG. 8).

One implication of knowing that a patient is going to soon suffer from sepsis is that one can apply an appropriate antibiotic therapy comprising a cocktail of the most potent drugs. Current clinical guidelines indicate that while waiting for culture results, a patient should be started on intravenous ceftriaxone and azithromycin. The purpose of this regimen is to try to avoid major resistance issues since only a portion of the patients who are thought to have the potential to acquire sepsis actually do so (see e.g. Table 3). Knowing that a patient has sepsis very early in the course of disease would enable physicians to prescribe the most aggressive therapies to try to reduce the influence of infection.

A second therapeutic strategy would be to try to break tolerance, reversing the immunosuppressive state of macrophages. To date virtually all therapies tried to treat sepsis have been in an attempt to do the opposite, i.e. suppress a hyperinflammatory state and this has the potential to worsen the patient's ability to defend against sepsis. Consistently, in more than 31 clinical trials to suppress the hyperinflammatory state, this approach has failed.

Examples of methods to break endotoxin tolerance include immune cells [Heusinkveld M, et al. Journal of Immunology 2011; 187:1157-1165], interferon gamma, CpG-ODN with or without IL-10, anti-CD40, inhibitors of STAT3, inhibitors of STATE, inhibitors of p50, inhibitors of NFκB, inhibitors of IKKβ, imidazoquinolines and zoledronic acid [Sica A, A Mantovani. Journal of Clinical Investigation 2012; 122:787-795]. Other potential agents include those chemical agents, cells or natural products that suppress the expression of one or more genes from the Endotoxin Tolerance Signature in M2 polarized macrophages, or to revert the properties of M2 macrophages in vitro and in vivo to those of an M1 macrophage [Sica and Mantovani, 2012].

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. A method for treating sepsis or decreasing the risk of sepsis-induced organ failure in a subject, the method comprising:
a) determining that the subject has sepsis, is at risk of developing sepsis, or at risk of sepsis-induced organ failure by:
(i) determining in a biological sample obtained from the subject a level of expression for each of a plurality of Endotoxin Tolerance Signature (ETS) genes wherein the plurality of ETS genes comprises C19orf59 and CYP1B1, said determining the level of expression does not comprise a microarray analysis,
(ii) producing a sample gene signature from the level of expression of the plurality of ETS genes, and
(iii) comparing the sample gene signature with a reference gene signature, wherein the reference gene signature represents a standard level of expression of each of the plurality of ETS genes to determine that there is a difference between the sample gene signature and the reference gene signature that indicates that the subject has sepsis, is at risk of developing sepsis, or is at risk of sepsis induced organ failure, and
b) administering to the subject an effective amount of one or more antibiotics, an agent that counteracts endotoxin tolerance, or both.

2. The method according to claim 1, wherein the one or more antibiotics is one or a combination of a glycopeptide, a cephalosporin, a beta-lactam, a beta-lactamase inhibitor, a carbapenem, a quinolone, a fluoroquinolone, an aminoglycoside, a macrolide and a monobactam.

3. The method according to claim 1, wherein the plurality of ETS genes further comprises one or more genes selected from the group consisting of CCL22, CD14, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINA1, UPP1, CPVL, CST3, LY86, and PROCR.

4. The method according to claim 1, wherein the plurality of ETS genes further comprises CCL22, CD14, CD300LF, DHRS9, FCER1G, FPR1, FPR2, GK, HISTH2H2AA3, HK2, HK3, HPSE, LILRA5, MGST1, PDLIM7, PLAUR, PSTPIP2, RAB13, RETN, RHBDD2, S100A4, S100A9, S100A12, SERPINAL UPP1, CPVL, CST3, LY86 and PROCR.

5. The method according to claim 1, wherein the agent that counteracts endotoxin tolerance is an immunotherapy, interferon gamma, a CpG-oligonucleotide (ODN), a combination of a CpG ODN with IL-10, an anti-CD40 antibody, an inhibitor of STAT3, an inhibitor of STAT6, an inhibitor of p50, an inhibitor of NFκB, an inhibitor of IKKβ, an imidazoquinoline or zoledronic acid.

6. The method according to claim 1, wherein the plurality of ETS genes consists of six ETS genes.

7. The method according to claim 1, wherein determining the level of expression comprises detecting nucleic acids encoded by each of the plurality of ETS genes.

8. The method according to claim 7, wherein determining the level of expression comprises one or more of a polymerase chain reaction (PCR) amplification method, a non-PCR based amplification method, reverse transcriptase-(RT) PCR, Q-beta replicase amplification, ligase chain reaction, signal amplification (Ampliprobe), light cycling, differential display, Northern analysis, DNA sequencing, RNA-Seq, MassArray analysis, and MALDI-TOF mass spectrometry.

9. The method according to claim 8, wherein determining the level of expression comprises a polymerase chain reaction (PCR) amplification method.

10. The method according to claim 1, wherein the biological sample comprises blood, plasma, serum, tissue, amniotic fluid, saliva, urine, stool, bronchoalveolar lavage fluid, cerebrospinal fluid or skin cells.

11. The method according to claim 10, wherein the biological sample comprises blood.

12. The method according to claim 1, wherein the plurality of ETS genes consists of C19orf59, CYP1B1, HK3, RETN, S100A8 and S100A12.

13. The method according to claim 1, wherein the plurality of ETS genes further comprises one or more genes selected from the group consisting of ADAM15, ADAMDEC1, ALCAM, ALDH1A1, ANKRD1, CA12, CAMP, CCL1, CCL19, CCL22, CCL24, CCL7, CD14, CD300LF, CD93, CDK5RAP2, CPVL, CST3, CST6, CTSK, CXCL10, CYP27B1, DDIT4, DHRS9, DPYSL3, EGR2, EMR1, EMR3, FBP1, FCER1G, FCER2, FPR1, FPR2, GK, GPNMB, GPR137B, HBEGF, HIST1H1C, HIST2H2AA3, HIST2H2AC, HK2, HK3 HPSE, HSD11B1, HTRA1, IL18BP, IL3RA, ITGB8, KIAA1199, LILRA3, LILRA5, LIPA, LY86, MARCO, MGST1, MMPI, MT1F, MT1G, MT1H, MT1M, MT1X, MXD1, MYADM, NEFH, NQO1, NRIP3, OLIG2, PANX2, PAPLN, PDLIM7, PLAUR, PLD3, PPBP, PROCR, PSTPIP2, PTGES, PTGR1, RAB13, RARRES1, RETN RHBDD2, RNASE1, S100A4, S100A8, S100A9, S100A12, SERPINA1, SERPINB 7, SLC16A10, SLC7A11, TGM2, TLR7, TMEM158, TREM1, TSPAN4, UPP1 and VCAN.

14. The method according to claim 1, wherein the plurality of ETS genes comprises C19orf59, CYP1B1, HK3, RETN, S100A8, and S100A12.

* * * * *